United States Patent [19]

Horii et al.

[11] Patent Number: 5,004,838

[45] Date of Patent: Apr. 2, 1991

[54] INOSOSE DERIVATIVES, PRODUCTION AND USE THEREOF

[75] Inventors: Satoshi Horii; Hiroshi Fukase, both of Osaka, Japan

[73] Assignee: Takeda Chemical Industries, Ltd., Osaka, Japan

[21] Appl. No.: 414,247

[22] Filed: Sep. 29, 1989

Related U.S. Application Data

[62] Division of Ser. No. 90,974, Aug. 31, 1987, Pat. No. 4,898,986.

[30] Foreign Application Priority Data

| Sep. 9, 1986 | [JP] | Japan | 61-212952 |
| Nov. 5, 1986 | [JP] | Japan | 61-263462 |
| Jan. 6, 1987 | [JP] | Japan | 62-779 |

[51] Int. Cl.$^5$ ............................................. C07C 45/45
[52] U.S. Cl. .................................................. 568/347
[58] Field of Search ....................................... 568/347

[56] References Cited

U.S. PATENT DOCUMENTS

| 2,768,965 | 10/1956 | Stansbury et al. | 568/347 |
| 3,387,003 | 6/1968 | Martel et al. | 568/347 |
| 3,454,600 | 7/1969 | Taub | 568/347 |
| 3,591,643 | 7/1969 | Fanta et al. | 568/347 |
| 4,446,319 | 5/1984 | Horii et al. | 564/462 |
| 4,486,602 | 12/1984 | Horii et al. | 564/462 |
| 4,777,294 | 11/1988 | Horii et al. | 564/462 |

FOREIGN PATENT DOCUMENTS 0063456 10/1982 European Pat. Off. ............ 564/462

OTHER PUBLICATIONS

S. Ogawa et al., "A Synthesis of DL-Penta-N-,O-Acetylvaliolamine," *Chemistry Letters*, pp. 1581-1582, 1985.

*Primary Examiner*—James H. Reamer
*Attorney, Agent, or Firm*—Wegner, Cantor, Mueller & Player

[57] ABSTRACT

Disclosed is a novel inosose compound represented by the general formula:

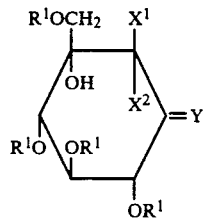

wherein $X^1$ and $X^2$ are both halogen; $X^1$ is hydrogen and $X^2$ is halogen; or $X^1$ is $-SQ^1$ and $X^2$ is $-SQ^2$ (each of $Q^1$ and $Q^2$ is lower alkyl or $Q^1$ and $Q^2$ may form lower alkylene), $R^1$ is a protective group for hydroxyl and Y is $=O$, $=N-Z$ (Z is hydroxyl which may be protected) or

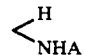

(A is hydrogen or an amine residue), particularly to the compound wherein the symbol Y is oxygen.

The inosose compound is useful as intermediates for production of valiolamine and the N-substituted derivatives thereof, which have potent α-glucosidase inhibiting activities and are useful as preventives or therapeutics for symptoms of hyperglycemia and various diseases derived therefrom in human and animals, such as diabetes, obesity and hyperlipemia.

1 Claim, No Drawings

INOSOSE DERIVATIVES, PRODUCTION AND USE THEREOF

This application is a divisional of U.S. Pat. Ser. No. 090,974, filed Aug. 31, 1987, now U.S. Pat. No. 4,898,986.

This invention relates to a novel inosose compound represented by the general formula:

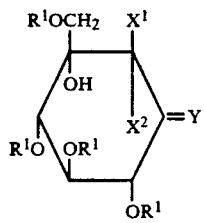

[I]

wherein $X^1$ and $X^2$ are both halogen, $X^1$ is hydrogen and $X^2$ is halogen, or $X^1$ is $-SQ^1$ and $X^2$ is $-SQ^2$ (each of $Q^1$ and $Q^2$ is lower alkyl or $Q^1$ and $Q^2$ may form a lower alkylene group), $R^1$ is a protective group for hydroxyl and Y is $=O$, $=N-Z$ (Z is hydroxyl which may be protected) or

(A is hydrogen or an amine residue), particularly to the compound [I] wherein the symbol Y is oxygen.

The compound [I] includes pseudohalosugar derivatives represented by the general formula:

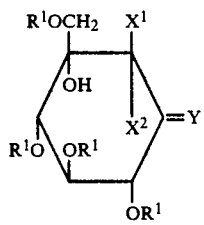

[I']

wherein $X^1$ and $X^2$ are both halogen; or $X^1$ is hydrogen and $X^2$ is halogen, and $R^1$ and Y are the same as above, and pseudosugar derivatives represented by the general formula:

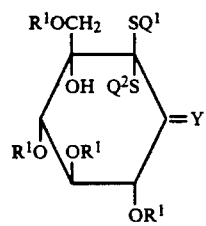

[I'']

wherein each of $Q^1$ and $Q^2$ is lower alkyl, or $Q^1$ and $Q^2$ may form lower alkylene, and $R^1$ and Y are the same as above.

This invention further relates to the production of the inosose compound [I], particularly of the compound [I] wherein the symbol Y is oxygen, and to the use of the inosose compound [I] for producing valiolamine and the derivatives thereof represented by the general formula:

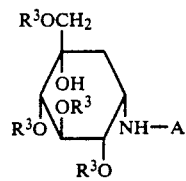

[II]

wherein $R^3$ is hydrogen or a protective group for hydroxyl and A is an amine residue or hydrogen.

The inosose compound [I] wherein $X^1$ and $X^2$ are both halogen; or $X^1$ is $-SQ^1$ and $X^2$ is $-SQ^2$ (each of $Q^1$ and $Q^2$ is lower alkyl or $Q^1$ and $Q^2$ may form lower alkylene), $R^1$ is a protective group for hydroxyl and Y is oxygen, can be prepared by treating a compound represented by the general formula:

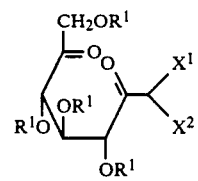

(4)

wherein $X^1$, $X^2$ and $R^1$ are the same as above, with a base.

The valiolamine and the derivatives thereof [II] can be produced by allowing a compound represented by the general formula:

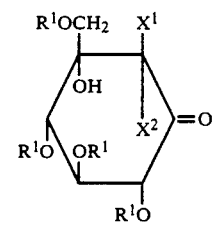

wherein $X^1$ and $X^2$ are both halogen, or $X^1$ is hydrogen and $X^2$ is halogen; $R^1$ is a protective group for hydroxyl, to react with a compound represented by the general formula: $R^2-NH_2$ wherein $R^2$ is an amine residue or hydroxyl which may be protected, followed by reduction, dehalogenation, and, if desired, removal of the protective group for hydroxyl and by allowing a compound represented by the general formula:

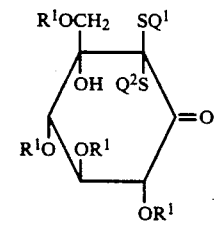

wherein $Q^1$ and $Q^2$ are both lower alkyl, or $Q^1$ and $Q^2$ may form lower alkylene; $R^1$ is a protective group for hydroxyl, to react with a compound represented by the general formula: $R^2-NH_2$ wherein $R^2$ is the same as above, followed by reduction, desulfurization, and, if desired, removal of the protective group for hydroxyl.

This invention furthermore relates to a process of preparing an inosose compound represented by the general formula:

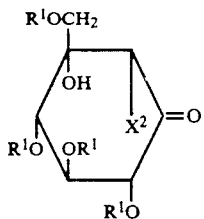
(6')

wherein $X^2$ is halogen and $R^1$ is a protective group for hydroxyl, which comprises subjecting a compound of the general formula:

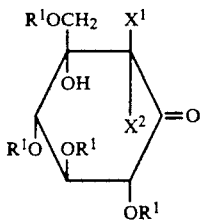
(5')

wherein $X^1$ and $X^2$ are both halogen, to partial dehalogenation, and a process of preparing an inosose compound represented by the general formula:

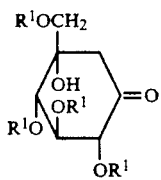
(12)

wherein $R^1$ is a protected group of hydroxyl, which comprises subjecting a compound represented by the general formula:

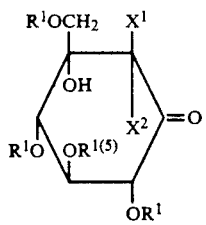

wherein $X^1$ and $X^2$ are both halogen; or $X^1$ is —$SQ^1$ and $X^2$ is —$SQ^2$ (each of $Q^1$ and $Q^2$ is lower alkyl or $Q^1$ and $Q^2$ may form lower alkylene) and $R^1$ is a protective group for hydroxyl, to dehalogenation or desulfurization.

Pseudoaminosugars such as valienamine, validamine, and valiolamine, and the N-substituted derivatives thereof, particularly the N-substituted derivatives of valiolamine, have potent α-glucosidase inhibiting activities [J. Med. Chem., 29, 1038–1046 (1986)], being useful compounds as preventives or therapeutics for symptoms of hyperglycemia and various diseases derived therefrom in human and animals, such as diabetes, obesity, and hyperlipemia. The said novel pseudosugar derivatives [I] are important compounds as the starting materials for production of valiolamine and the N-substituted derivatives thereof.

Known methods for production of valiolamine include isolation from the culture broth of *Streptomyces hygroscopicus* subsp. *limoneus* [EP 0063456, 1984.8.1], and syntheses starting from valienamine or validamine obtained by degradation of validamycins [U.S. Pat. No. 4,446,319, 1984.5.1]. In addition, a method of synthesis of DL-penta-N,O-acetylvaliolamine via DL-1,2,3-tri-O-acetyl-(1,3/2,4)-4-bromo-6-methylene-1,2,3-cyclohexanetriol [S. Ogawa et al., Chem Lett., 1581–1582 (1985)] has also been reported.

The method for producing valiolamine directly by fermentation is the most convenient and simplest, while this method has a problem of yield from the view point of industrial application. The method to produce valiolamine via valienamine is an excellent industrial procedure, while the method has a disadvantage that valienamine produced is comparatively costly because the molecular weight of the constituent valienamine is only about 1/2.7 of the molecular weight of validamycin A, one of the starting materials. The method of production by chemical synthesis by S. Ogawa et al. has a problem to be solved in the process of resolution of the stereoisomers (DL-isomers). Thus more industrially advantageous methods of production of valiolamine than these known methods had been sought.

As a result of the researches by the inventors to solve the problems described above, the inventors succeeded in the synthesis of valiolamine and its N-substituted derivatives via the compounds represented by the general formula [I] from 1-C-(1,3-dithian-2-yl)-D-glucopyranose derivatives; 1-C-[bis((lower alkyl)thio)-methyl]-D-glucopyranose derivatives such as 1-C-[bis(-methylthio)methyl]-D-glucopyranose derivatives and 1-C-[bis(ethylthio)methyl]-D-glucopyranose derivatives; 1-C-(dihalomethyl)-D-glucopyranose derivatives such as 1-C-(dichloromethyl)-D-glucopyranose derivatives and 1-C-(dibromomethyl)-D-glucopyranose derivatives. These derivatives were obtained by lengthening of the carbon chain of the D-glucono-δ-lactone derivatives of which the hydroxyl groups at 2-, 3-, 4-, and 6-position are protected by hydroxyl-protective groups, which can be produced readily from easily available and inexpensive D-glucose or D-glucono-δ-lactone (D-gluconic acid 6-lactone), with 2-lithio-1,3-dithiane; bis[(lower alkyl)thio]methyllithiun such as bis(methylthio)methyllithium and bis(ethylthio)methyllithium; dihalomethyllithium such as dichloromethyllithium and dibromomethyllithium. The processes for producing the compound [I] and the preparation of valiolamine and its derivatives [II] from the compound [I] are explained in the concrete below and the processes are also illustrated below.

First, the processes for producing the compound [I'] (the compound of the general formula [I] wherein $X^1$ and $X^2$ are both halogen, or $X^1$ is hydrogen and $X^2$ is halogen) and the preparation of valiolamine and the derivatives thereof [II] from the compound [I'] are illustrated in FIG. 1 and FIG. 2, and subsequently, the processes for producing the compound [I''] (the compound of the general formula [I] wherein $X^1$ is $SQ^1$ and $X^2$ is $SQ^2$) and the preparation of valiolamine and the derivatives thereof [II] from the compound [I''] are illustrated in FIG. 3 and FIG. 4.

Processes for preparing the pseudohalosugar derivatives [I'] and valiolamine and the derivatives thereof [II]:

In FIG. 1 and FIG. 2, $R^1$ is a protective group for hydroxyl, $R^3$ is a protective group for hydroxyl or hydrogen, X is halogen, $X^1$ and $X^2$ are both halogen, or $X^1$ is hydrogen and $X^2$ is halogen, Z is a hydroxyl group which may be protected, and A is an amine residue or hydrogen.

FIG. 1

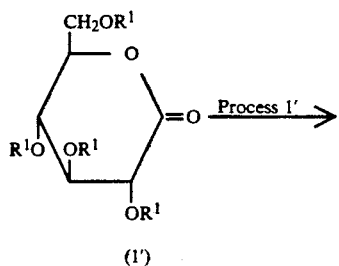

(1')

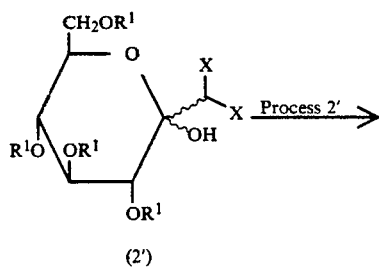

(2')

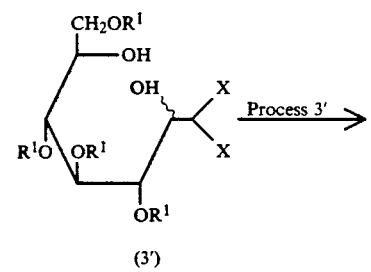

(3')

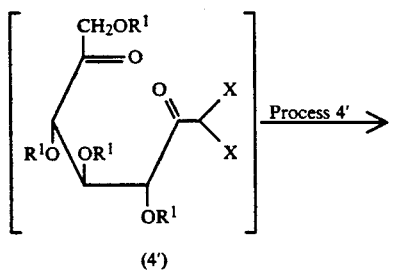

(4')

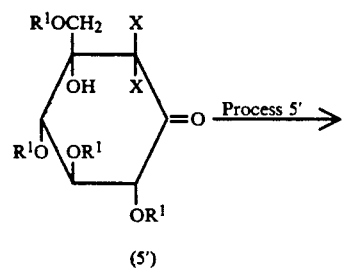

(5')

FIG. 2

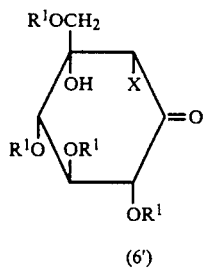

(6')

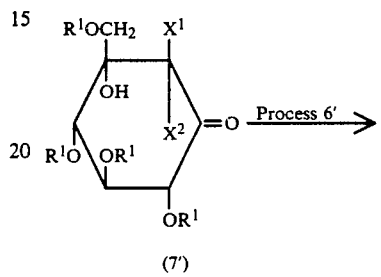

(7')

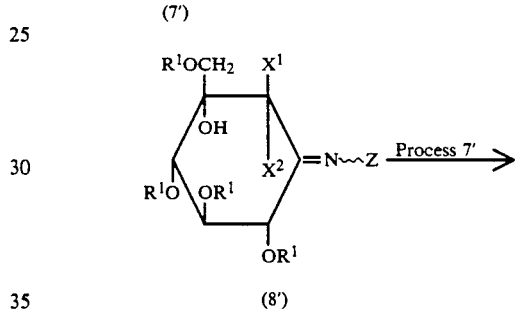

(8')

(9')

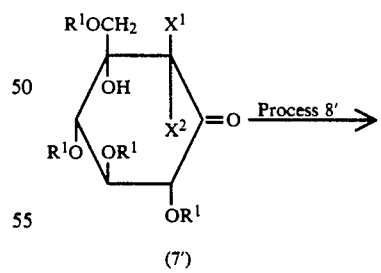

(7')

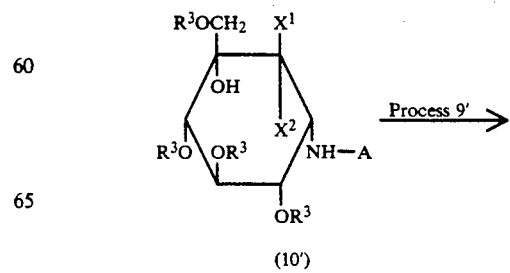

(10')

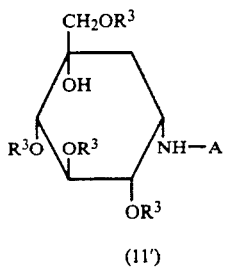

(11')

The compound (7') in FIG. 2 can be synthesized via the following processes 1'-5' starting from D-glucono-δ-lactone derivative (1'), i.e.

Process 1': a process to produce 1-C-(dihalomethyl)-D-glucopyranose derivative, namely 1-deoxy-1,1-dihalo-D-gluco-2-heptulose derivative (2'), such as 1-C-(dichloromethyl)-D-glucopyranose derivative and 1-C-(dibromomethyl)-D-glucopyranose derivative, by the reaction of dihalomethyl carbanion such as dichloromethyl carbanion and dibromomethyl carbanion obtained by treatment of dihalomethane such as dichloromethane and dibromomethane with a base such as lithium diisopropylamide and lithium dicyclohexylamide, with D-glucono-δ-lactone derivative (1'), Process 2': a process to produce 1-C-(dihalomethyl)-D-glucitol derivative (3') by opening of the pyranose ring by reduction of the hemiketal-forming carbonyl group into a hydroxyl group, Process 3': a process to produce dioxo derivative (4') by oxidation of the hydroxyl groups at 1- and 5-positions of the glucitol derivative (3'), Process 4': a process to produce (1S)-(1(OH),2,4/1,3)-1-C-(hydroxymethyl)-6,6-dihalo-5-oxo-1,2,3,4-cyclohexanetetrol derivative (5') such as (1S)-(1(OH),2,4/1,3)-1-C-(hydroxymethyl)-6,6-dichloro-5-oxo-1,2,3,4-cyclohexanetetrol derivative and (1S)-(1(OH),2,4/1,3)-1-C-(hydroxymethyl)-6,6-dibromo-5-oxo-1,2,3,4-cyclohexanetetrol derivative by the reaction of the compound (4') with a base, that is, Processes 2'-4' to produce (1S)-(1(OH),2,4/1,3)-1-C-(hydroxymethyl)-6,6-dihalo-5-oxo-1,2,3,4-cyclohexanetetrol derivative (5') from 1-deoxy-1,1-dihalo-D-gluco-2-heptulose derivative (2'), via 1-C-(dihalomethyl)-D-xylo-5-hexosulose derivative which is obtained by oxidation of the hydroxyl group at 6-position of the compound (2') into oxo group, i.e. 1-deoxy-1,1-dihalo-D-xylo-2,6-heptodiulose derivative (4') as the intermediate, and Process 5': a process to produce (1S)-(1(OH),2,4/1,3)-1-C-(hydroxymethyl)-6-monohalo-5-oxo1,2,3,4-cyclohexanetetrol derivative (6') such as (1S)-(1(OH),2,4/1,3)-1-C-(hydroxymethyl)-6-chloro-5-oxo-1,2,3,4-cyclohexanetetrol derivative and (1S)-(1(OH),2,4/1,3)-1-C-(hydroxymethyl)-6-bromo-5-oxo-1,2,3,4-cyclohexanetetrol derivative by partial dehalogenation of the compound (5'), if necessary.

The dioxo derivative (4') produced in Process 3', being very reactive compound usually reacts with a base which is used in excess in the oxidation reaction (Process 3'), to cause cyclization reaction (Process 4'), and thus the compound (5') is produced apparently in one step from the compound (3').

Valiolamine and the derivatives thereof can be produced from the compound (7') as shown in FIG. 2, i.e. from the compound (5') or (6') in FIG. 1.

That is, valiolamine and its O-substituted derivative (9') (the compound of the general formula [II] wherein A is a hydrogen atom) can be synthesized via Process 6': a process to produce the oxime derivative or the O-substituted oxime derivative (8') such as O-alkyloxime and O-aralkyloxime derivative of the compound (7') by the reaction of the compound (7') with the compound represented by the general formula Z-NH₂ (wherein Z is a hydroxyl group which may be protected) such as hydroxylamine and O-substituted hydroxylamine including O-methylhydroxylamine and O-benzylhydroxylamine, and Process 7': a process of dehalogenation of the compound (8') to eliminate the halogen atom (Process 7a'), a process to reduce the hydroxyimino group of the oxime into an amino group (Process 7b'), and, if necessary, a process to remove the protective group (Process 7c').

The N-substituted derivative (11') of valiolamine (the compound of the general formula [II] wherein A is an amine residue) can be synthesized via Process 8': a process to produce the compound (10') by the reaction of the compound (7') with a primary amine represented by the general formula R²-NH₂ (wherein R² is an amine residue) followed by reduction of the resulting Schiff's base, and Process 9': a process of dehalogenation of the compound (10') to eliminate the halogen atom followed by, if necessary, removal of the protective group.

Process 1', i.e. a process to produce 1-C-(dihalomethyl)-D-glucopyranose derivative (2') from D-glucono-δ-lactone derivative (1'), is conducted by allowing the compound (1') to react with dihalomethyllithium. As appropriate solvents for this reaction, those which are inactive to this reaction, such as tetrahydrofuran, 1,4dioxane, ethyl ether, and hexane, and an excess of dihalomethane (e.g. dichloromethane, dibromomethane) which is used as the starting material to produce dihalomethyllithium are used separately or in combination as a mixed solvent. This reaction is conducted preferably in an atmosphere of inert gas such as nitrogen and argon. Reaction temperature is usually 0° C.--110° C., preferably −50° C. --78° C. in the initial stage of the reaction and −20° C. --40° C. in the later stage Reaction time is appropriately about 1-8 hours.

In Process 2'the reduction of the hemiketal-forming carbonyl group of the compound (2') into a hydroxyl group can be effected by using, complex metal hydrides as a reducing agent, in the concrete, a alkali metal borohydride such as sodium borohydride and potassium borohydride, or a alkali metal cyanoborohydride such as sodium cyanoborohydride. However it should be noted that in this reaction only the hemiketal-forming carbonyl group is necessary to be reduced into a hydroxyl group under the condition which does not give rise to reductive dehalogenation. A desirable example of the reduction under such condition is: the compound (2') is dissolved in an anhydrous ether such as tetrahydrofuran, dioxane, diethylene glycol dimethyl ether and ethyl ether, and a reducing agent described above is suspended in this solution and stirred.

Reaction temperature of the reduction varies depending upon the reducing agent used, and it is usually −30° C. -40° C., but occasionally, particularly at the initial stage, the reaction is conducted under cooling to about −78° C., or by heating to about 80° C. Reaction time also varies depending upon the reducing agent used and reaction temperature, but reaction time usually for several minutes to about 24 hours for this purpose.

In the Process 3', for the reaction to produce the dioxo derivative (4') by oxidation of the unprotected hydroxyl groups of the alditol derivative (3'), the reaction condition for oxidation of the secondary hydroxyl group in sugars or polyhydric alcohols into a carbonyl group is employed. For example, the oxidation is effected by using dimethyl sulfoxide and its activating agent, such as dimethyl sulfoxide and trifluoroacetic anhydride, dimethyl sulfoxide and acetic anhydride, dimethyl sulfoxide and phosphorus pentoxide, dimethyl sulfoxide and sulfur trioxide-pyridine complex, dimethyl sulfoxide and oxalyl chloride, preferably dimethyl sulfoxide and trifluoroacetic anhydride. An oxidation reaction may be effected by using chromium trioxide-pyridine complex, pyridinium dichromate, nicotinium dichromate, or ruthenium (VIII) oxide.

The reaction condition varies depending upon the oxidizing agent used. As the solvent for the reaction, dichloromethane, chloroform, benzene, toluene, dimethyl formamide, dimethyl sulfoxide and acetic anhydride are used separately or in combination. The reaction is conducted usually at $-10°$ C.–$40°$ C., occasionally by cooling to about $-78°$ C., particularly in the initial stage of the reaction The reaction time is about 1 to 24 hours.

Bases used in the reaction of Process 4'to produce inosose derivative (5') by intramolecular cyclization reaction of 1-C-(dihalomethyl)-D-xylo-5-hexosulose derivative (4') with a base include trialkyl($C_{1-6}$)amines such as trimethylamine, triethylamine, tri-n-propylamine, and tri-n-butylamine, salts of alkali metals such as potassium acetate, sodium acetate, potassium carbonate, sodium carbonate, and potassium hydrogencarbonate, alkali metal hydroxides such as potassium hydroxide and sodium hydroxide, alkali metal hydrides such as sodium hydride, potassium hydride and lithium hydride, alkali metal alkoxides such as sodium methoxide, sodium ethoxide, and potassium tert-butoxide, and alkyl alkali metals such butyllithium and propyllithium. The reaction solvent varies depending on the base used, and aromatic hydrocarbons such as benzene and toluene, ethers such as tetrahydrofuran, ethylene glycol monoethyl ether, and ethyl ether are used advantageously. The reaction temperature also varies depending on the base used and the solvent used, being usually $10°$ C. to the boiling point of the solvent, and occasionally, particularly in the initial stage of the reaction, the reaction is conducted by cooling to about $-78°$ C. The reaction time also varies depending on the reaction temperature, being usually about 1 to about 18 hours.

The dioxo derivative (4') produced in Process 3', being very reactive, usually reacts with a base, when the base is used in excess as a reagent for oxidation, to cause a cyclization reaction (Process 4'), and thus apparently the compound (5') is produced in one step.

Methods to eliminate only the halogen atom in Process 5'without affecting the carbonyl group of the dihalopseudoinosose derivative (5') include the method of reductive dehalogenation of $\alpha,\alpha$-dihaloketones to produce the corresponding $\alpha$-monohaloketones or the parent ketones [e.g. see a review by R. Noyori and Y. Hayakawa in Organic Reactions, Vol.29, Chart 2, in particular pp 180–182]. For example, the method of dehalogenation with zinc dust in a protic solvent such as acetic acid is preferably employed. The conditions of this reaction to derive monohalo derivative (6') from dihalo derivative (5') vary depending upon the halogen and the hydroxyl-protective group in the compound (5'); for example, the reaction temperature is about $10°$–$30°$ C. and the reaction time is about 30 minutes to about 3 hours.

In Processes 6'and 7'wherein the compound (7'), i.e. the compound (5') or the compound (6'), is allowed to react with a hydroxylamine in which the hydroxyl group may be protected, followed by reduction of the resulting oxime and, if necessary, by removal of the protective group, to produce valiolamine, the reduction of oxime can be effected, for example, by catalytic reduction in an appropriate solvent in the presence of a platinum catalyst such as platinum oxide, a palladium catalyst such as palladium black and palladium carbon, a nickel catalyst such as Raney nickel, or a rhodium catalyst such as rhodium carbon, or by using an aluminum hydride derivative such as lithium aluminum hydride, preferably in the atmosphere of an inert gas such as nitrogen and argon. Reduction of oximes into amino compounds may be effected before and after the removal of hydroxyl-protective groups in the cyclitol moiety.

In Process 8', the condensation of the compound (7') with a primary amine (a compound of the general formula $R^2$—$NH_2$ wherein $R^2$ is an amine residue) and the reduction of the resulting Schiff's base are effected generally in solvents. As appropriate solvents, polar solvents including water, alcohols such as methanol, ethanol, propanol, and butanol; acetonitrile, dimethyl sulfoxide, N,N-dimethylformamide, and N-methylacetamide; glymes such as methyl cellosolve, dimethyl cellosolve, and diethylene glycol dimethyl ether, and ethers such as dioxane, tetrahydrofuran and ethyl ether, are used separately or in combination with each other, or in combination of the above-mentioned solvents and nonpolar solvents such as benzene, toluene, and ethyl acetate.

The reaction temperature of the formation of the Schiff's base is not specified, being usually room temperature to about $100°$ C. The reaction time varies depending upon reaction temperature, usually several minutes to about 24 hours being enough to attain the purpose.

For reduction of the Schiff's base formed, are used advantageously various metal hydride complex reducing agents including alkali metal borohydrides such as sodium borohydride, potassium borohydride, lithium borohydride, and sodium methoxyborohydride, alkali metal cyanoborohydrides such as sodium cyanoborohydride, alkali metal aluminum hydrides such as lithium aluminum hydride, and dialkylamine boranes such as dimethylamine borane. When sodium cyanoborohydride is used, the reaction is preferably conducted under acidic condition, for example in the presence of hydrochloric acid, acetic acid or the like.

Reaction temperature of this reduction varies depending on the Schiff's base and the reducing agent used, being usually $0°$ C.–$40°$ C., occasionally the reaction is conducted under cooling to about $0°$ C.–$-20°$ C. or by heating to about $100°$ C. Reaction time also varies depending upon the reaction temperature, Schiff's base to be reduced, and the reducing agent, usually several minutes to about 24 hours being enough to attain the purpose.

Reduction of the Schiff's base formed may be effected by means of catalytic reduction. That is, reduction can be effected by shaking or stirring the Schiff's base in an appropriate solvent in the presence of a catalyst for catalytic reduction in a stream of hydrogen. Catalysts for catalytic reduction include platinum black, platinum dioxide, palladium black, palladium carbon, and Raney nickel. Solvents used usually include water; alcohols such as methanol and ethanol; ethers such as dioxane and tetrahydrofuran, and N,N-dimethylformamide, which are used separately or in combination. The reaction is carried out usually at 0° C.–40° C. at atmospheric pressure, but may be carried out by applying pressure or by heating.

Dehalogenation of the pseudohalosugar derivative represented by the general formulas (8′) and (10′) in Processes 7′and 9′can be effected by reductive dehalogenation for example by catalytic reduction. That is, the reaction is conducted by shaking or stirring the compound represented by the general formulas (8′) and (10′) with hydrogen in an appropriate solvent in the presence of a catalyst for catalytic reduction. Catalysts for catalytic reduction include palladium carbon, palladium black, Raney nickel, platinum black and platinum dioxide. The solvent used is selected on the basis of the solubility of the pseudohalosugar derivative and of the compound formed by the dehalogenation, and usually water, alcohols such as methanol and ethanol, ethers such as tetrahydrofuran and dioxane, and dimethylformamide are used separately or in combination. The reaction is carried out at atmospheric pressure or an elevated pressure, usually at 0°–40° C. for about 2–48 hours As reductive dehalogenating agents, are used advantageously various metal hydride complex reducing agents including borohydride complex reducing agents such as sodium borohydride, potassium borohydride, lithium borohydride, sodium trimethoxyborohydride, and sodium triethylborohydride. Solvents for the reaction include water, alcohols such as methanol, ethanol, propanol, and butanol; N,N-dimethylformamide, N-methylacetamide, and dimethyl sulfoxide; glymes such as methyl cellosolve, dimethyl cellosolve, and diethylene glycol dimethyl ether; ethers such as dioxane and tetrahydrofuran, and acetovarious nitrile, which are used separately or in combination with each other, or in combination with nonpolar solvents such as ethyl acetate and benzene. Reaction condition varies depending upon the reducing agent used; reaction temperature is usually 0°–40° C., and occasionally the reaction is carried out by heating to the reflux temperature of the solvent. Reaction time also varies depending upon the reaction temperature and the reducing agent used, usually 1 to 24 hours being enough to attain the purpose.

Reductive dehalogenation may be effected by using organic tin hydrides. That is, the desired product can be obtained by dissolving or suspending in an aromatic organic solvent such as benzene, toluene, and xylene, or in a aliphatic organic solvents such as ethyl ether, dioxane, and diethylene glycol monoethyl ether, followed by addition of an organic tin hydride such as (n-$C_4H_9)_3SnH$, n-($C_4H_9)_2SnH_2$, (n-$C_3H_7)_3SnH$, ($C_2H_5)_3SnH$, ($C_6H_5)_3SnH$, and ($C_6H_5)_2SnH_2$ and an initiator of radical reaction (for example, azo compounds such as α,α′-azobisisobutyronitrile, peroxides such as benzoyl peroxide, and triphenyl borate), preferably α,α′-azobisisobutyronitrile. The reaction is carried out usually at 10°–150° C. for about 1–24 hours.

In addition a method of reductive dehalogenation using metal aluminum hydride complexes such as lithium aluminum hydride, sodium aluminum hydride, sodium aluminum triethoxyhydride, sodium aluminum bis(2-methoxyethoxy)hydride, and sodium aluminum diethylhydride; a method based on reaction with sodium or lithium in liquid ammonia; a method of reductive dehalogenation with zinc and hydrochloric acid or acetic acid; and a method of dehalogenation based on electrolytic reduction may be used.

The compounds (5′), (6′), (7′), (8′), and (10′), namely the compound [I′], are all novel pseudohalosugar derivatives and important as the intermediates for production of the desired useful compounds (9′) and (11′), namely the compound [II].

Processes for preparing the pseudosugar derivatives [I″] and valiolamine and the derivatives thereof [II]

In FIG. 3 and FIG. 4, each of $Q^1$ and $Q^2$ is lower alkyl, or $Q^1$ and $Q^2$ may form lower alkylene, $R^1$ is a protective group for hydroxyl, $R^3$ is a protective group for hydroxyl or hydrogen, Z is a hydroxyl group which may be protected and A is an amine residue or hydrogen.

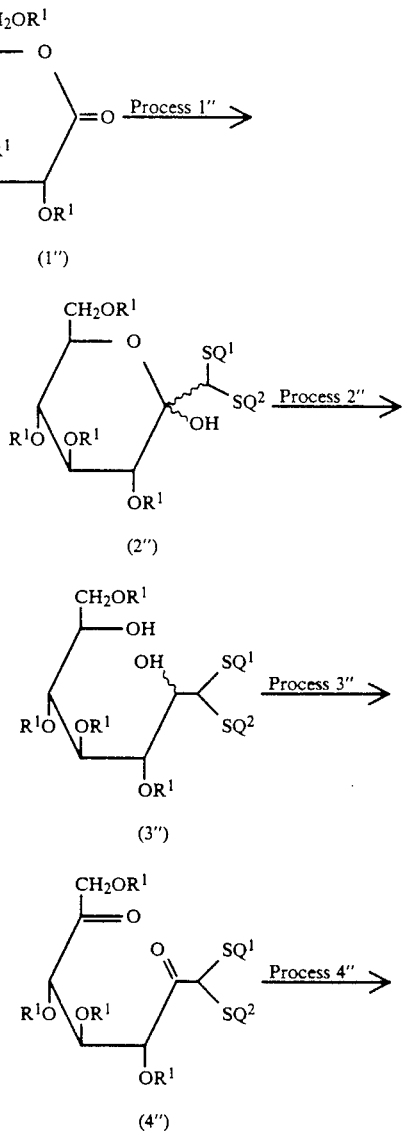

FIG. 3

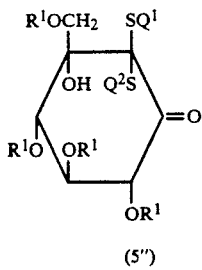

(5″)

FIG. 4

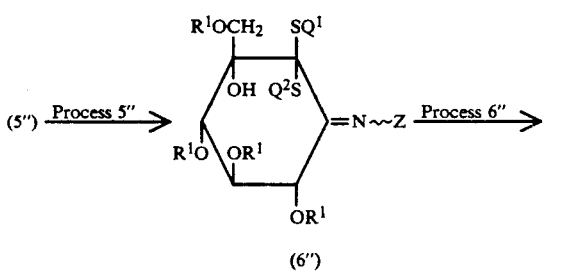

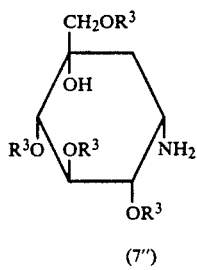

(7″)

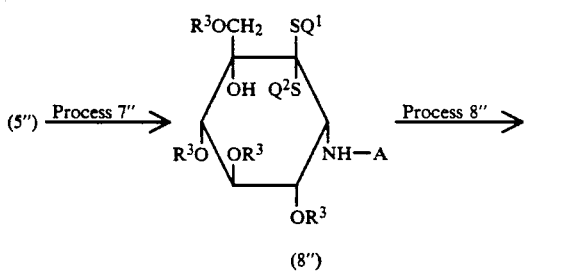

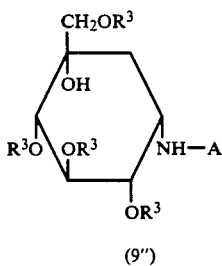

(9″)

The compound represented by the general formulas [I″] and [II] can be produced via the compound (2″) obtained by the reaction of D-glucono-δ-lactone derivative (1″) with a carbanion represented by the general formula:

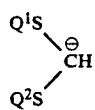

The carbanions represented by the general formula described above include carbanions wherein $Q^1$ and $Q^2$ are independently lower alkyl($C_{1-3}$) groups such as methyl, ethyl, propyl and isopropyl, in the concrete, carbanions derived from, for example, bis(methylthio)methane and bis(ethylthio)methane, and compounds wherein $Q^1$ and $Q^2$ represent together a lower alkylene($C_{2-3}$) group such as ethylene and trimethylene, in the concrete, carbanions derived from, for example, 1,3-dithiolane and 1,3-dithiane. The processes 1″–4″ for production of compound (5″) from compound (1″) and the process 5″–8″ for production of compounds (7″) and (9″) from compound (5″) are described in FIG. 3 and 4 for an easier understanding, in which carbanions derived from bis(methylthio)methane and 1,3-dithiane were used as typical and desirable examples of the carbanion shown by the general formula described above. Namely the compound (5″) can be synthesized via Processes 1″–4″, that is, Process 1″: (i) a process of producing D-gluco-2-heptosulose (2,6) 1,1-(dimethyl dithioacetal) with the hydroxyl groups at 3-, 4-, 5-, and 7-positions protected, that is, 1-C-[bis(methylthio)methyl]-D-glucopyranose derivative (2″), by the reaction of a carbanion obtained by treatment of bis(methylthio)methane with a base such as n-butyllithium, with D-glucono-δ-lactone derivative (1″), or (ii) a process of producing D-gluco-2-heptosulose (2,6) 1,1-(trimethylene dithioacetal) of which the hydroxyl groups at 3-, 4-, 5-, and 7-positions were protected, that is, 1-C-(1,3-dithian-2-yl)-D-glucopyranose derivative (2″), by the reaction of a carbanion obtained by treatment of 1,3-dithiane with a base such as n-butyllithium, with D-glucono-δ-lactone derivative (1″), Processes 2″ and 3″: a process of producing of 1-C-bis(methylthio)methyl-D-xylo-5-hexosulose derivative or 1-C-(1,3-dithian-2-yl)-D-xylo-5-hexosulose derivative (4″) by oxidation of the hydroxyl group at 6-position of D-gluco-2-heptosulose derivative (2″) into an oxo group, that is, Process 2″ to produce 1-C-bis(methylthio)methyl-D-glucitol derivative or 1-C-(1,3-dithian-2-yl)-D-glucitol derivative (3″) by ring opening of the pyranose ring by reduction of the hemiketal-forming carbonyl group of the compound (2″) into a hydroxyl group, and Process 3″ to produce the dioxo derivative (4″) by oxidation of the hydroxyl groups at 1- and 5-positions of the glucitol derivative (3″), and Process 4″: a process to produce (1S)-(1(OH),2,4/1,3)-1-C-(hydroxymethyl)-5-oxo-6,6-bis(-methyl-thio)-1,2,3,4-cyclohexanetetrol derivative or (1S)-(1(OH), 2,4/1,3)-1-C-(hydroxymethyl)-5-oxo-6,6-(trimethylenedithio)-1,2,3,4-cyclohexanetetrol derivative (5″) by treatment of the compound (4″) with a base.

Valiolamine and the derivatives thereof can be produced, for example, from the compound (5″) as shown in FIG. 4. That is, valiolamine and the O-substituted derivative (7″) can be synthesized via Process 5″: processes to produce the oxime derivative or the O-substituted oxime derivative (6″), including O-alkyl oxime and O-aralkyl oxime derivative of the compound (5″), by the reaction of the compounds (5″) with the compound represented by the general formula $Z-NH_2$ (wherein Z is hydroxyl group which may be protected), such as hydroxylamine and O-substituted hydroxylamines, for example O-methylhydroxylamine and O-benzylhydroxylamine, and Process 6″ a process of desulfurization of the compound (6″) to eliminate the bis(methylthio) group or trimethylenedithio group (Process 6a″), a process to reduce the hydroxyimino group of the oxime into an amino group (Process 6b″), and, if necessary, a process to remove the protective group (Process 6c″).

The N-substituted derivative (9″) of valiolamine (the compound of the general formula [II] wherein A is an amine residue) can be synthesized via Process 7″: a process to produce the compound (8″) by the reaction of the compound (5″) with a primary amine represented by the general formula $R^2$—$NH_2$ (wherein $R^2$ is an amine residue) followed by reduction of the resulting Schiff's base, and Process 8″: a process of desulfurization of the compound (8″) to eliminate the bis(methylthio) group or the trimethylenedithio group, and, if necessary, a process to remove the protective groups.

Process 1″, i.e. a process to produce, for example, 1-C-[bis(methylthio)methyl]-D-glucopyranose derivative (2″) from D-glucono-δ-lactone derivative (1″), is conducted by allowing the compound (1″) to react with bis(methylthio)methyllithium, or a process to produce 1-C-(1,3-dithian-2-yl)-D-glucopyranose (2″), is conducted by allowing the compound (1″) to react with 2-lithio-1,3-dithiane. In this reaction, usually 1 to 5 mole equivalents, preferably 2-2.5 mole equivalents, of bis(methylthio)methyllithium or 2-lithio-1,3-dithiane for D-glucono-δ-lactone derivative (1″) is used. This reaction is conducted in an appropriate solvent which is inactive to this reaction, such as tetrahydrofuran, 1,4-dioxane, ethyl ether, and hexane, which are used separately or in combination, preferably in an atmosphere of an inert gas such as nitrogen and argon. Reaction temperature is usually $-20°$ C. $-{-78}°$ C., preferably $-50°$ C.$-{-78}°$ C. in the initial stage of the reaction and $-20°$ C.$-{-40}°$ C. in the later stage. Reaction time is appropriately about 1-8 hours.

In Process 2″, in the reduction of the hemiketal forming carbonyl group of the compound (2″) into a hydroxyl group, desirable reducing agents for reduction with a reducing agent include metal hydrogen complexes, diborane, and substituted diboranes. In the concrete, are included metal borohydrides such as sodium borohydride, potassium borohydride, lithium borohydride, zinc borohydride, sodium trimethoxyborohydride, potassium tri-sec-butylborohydride, lithium tri-sec-butylborohydride, sodium tri-sec-butylborohydride, potassium trisiamylborohydride and lithium trisiamylborohydride, alkali metal cyanoborohydrides such as sodium cyanoborohydride and tetra-n-butylammonium cyanoborohydride, alkali metal aluminum hydrides such as lithium aluminum hydride, lithium trimethoxyaluminum hydride, and lithium tri(tert-butoxy)aluminum hydride, alkyl boranes such as 2,3-dimethyl-2-butylborane, bis-3-methyl-2-butylborane, diisopinocamphenylborane, dicyclohexylborane, 9-borabicyclo[3.3.1]nonane, and N,B-enantrane, and alkylamine boranes such as dimethylamine borane and tetramethylammonium borohydride.

Reaction temperature of these reduction varies depending upon the reducing agents used, being usually $-30°$ C.$-40°$ C., but occasionally, particularly in the initial stage of the reduction, the reaction is conducted under cooling to about $-78°$ C., or by heating to about 80° C. Reaction time also varies depending upon the reducing agent used and reaction temperature, but usually reaction for several minutes to about 24 hours can attain the goal.

In the Process 3″, for the reaction to produce the dioxo derivative (4″) by oxidation of the unprotected hydroxyl group of the alditol derivative (3″), the reaction condition for oxidation of the secondary hydroxyl group in sugars or polyhydric alcohols into a carbonyl group is employed. That is, oxidation is effected by using dimethyl sulfoxide and its activating agent, such as dimethyl sulfoxide and trifluoroacetic anhydride, dimethyl sulfoxide and acetic anhydride, dimethyl sulfoxide and phosphorus pentoxide, dimethyl sulfoxide and sulfur trioxide-pyridine complex, dimethyl sulfoxide and oxalyl chloride, preferably dimethyl sulfoxide and trifluoroacetic anhydride. Oxidation may be effected by using chromium trioxide-pyridine complex, pyridinium dichromate, nicotinium dichromate, or ruthenium (VIII) oxide.

The reaction condition varies depending upon the oxidizing agents used. As the solvent for the reaction, dichloromethane, chloroform, benzene, toluene, dimethyl formamide, dimethyl sulfoxide and acetic anhydride are used separately or in combination. The reaction is conducted usually at $-10°$ C.$-40°$ C., occasionally by cooling to about $-78°$ C. particularly in the initial stage of the reaction Reaction time is about 1 to 24 hours.

Bases used in the reaction of Process 4″ to produce polyhydroxy substituted cyclohexanone derivative, i.e. inosose derivative (5″) by intramolecular cyclization reaction of 1-C-bis(methylthio)methyl-D-xylo-5-hexosulose derivative or 1-C-(1,3-dithian-2-yl)-D-xylo-5-hexosulose derivative (4″) with a base include salts of alkali metals such as potassium acetate, sodium acetate, potassium carbonate, sodium carbonate, and potassium hydrogencarbonate, alkali metal hydroxides such as potassium hydroxide and sodium hydroxide, alkali metal hydrides such as sodium hydride, potassium hydride and lithium hydride, alkali metal alkoxides such as sodium methoxide, sodium ethoxide, and potassium tert-butoxide, and alkyl alkali metals such as butyllithium and propyllithium. For the intramolecular cyclization reactions using bases from the compound (4″) to the compound (5″), desirable methods include those using alkali metal carbonates such as potassium carbonate and sodium carbonate as the base in the presence of crown ether such as 18-crown-6, dibenzo-18-crown-6, dicyclohexyl-18-crown-6, and 15-crown-5 [Reference: P. A. Aristoff, Synthetic Communication, 13, 145-150 (1983)]. The reaction solvent varies depending on the base used, and aromatic hydrocarbons such as benzene and toluene, ethers such as tetrahydrofuran, ethylene glycol monoethyl ether, and ethyl ether are used advantageously. The reaction temperature also varies depending on the base used and the solvent used, being usually 10° C. to the boiling point of the solvent, and occasionally, particularly in the initial stage of the reaction, the reaction is conducted by cooling to about $-78°$ C. The reaction time also varies depending on the reaction temperature, being usually about 1 to about 18 hours.

In the process for producing valiolamine by subjecting the oxime (6″) obtained by the reaction of the compound (5″) with hydroxylamine of which hydroxyl group may be protected, to desulfurization of the bis(methylthio) group or the trimethylenedithio group, and by reduction of the hydroxyimino group of which hydroxyl group may be protected into an amino group, and, if necessary, by removal of the protective group, the reduction of oxime into amine can be effected, for example, by catalytic reduction in an appropriate solvent in the presence of a platinum catalyst such as platinum oxide, a palladium catalyst such as palladium black and palladium carbon, a nickel catalyst such as Raney nickel, or a rhodium catalyst such as rhodium carbon, or by reduction using an aluminum hydride derivative such as lithium aluminum hydride, preferably in the atmosphere of an inert gas such as nitrogen and argon. Reduction of oximes into amino compounds may be effected before or after removal of the hydroxyl-protective groups in the cyclitol moiety.

In Process 7", condensation of the compound (5") with a primary amine (a compound or the general formula $R^2$—$NH_2$ wherein $R^2$ is an amine residue) and the reduction of the resulting Schiff's base are conducted generally in solvents As appropriate solvents, polar solvents including water, alcohols such as methanol, ethanol, propanol, and butanol; acetonitrile, dimethyl sulfoxide, N,N-dimethylformamide, N-methylacetamide; glymes such as methyl cellosolve, dimethyl cellosolve, and diethylene glycol dimethyl ether, and ethers such as dioxane, tetrahydrofuran and ethyl ether, are used separately or in combination with each other as a mixed solvent, or in combination of the above mentioned solvents with a nonpolar solvent such as benzene, toluene, and ethyl acetate.

The reaction temperature of the formation of the Schiff's base is not specified, being usually room temperature to about 100° C. The reaction time varies depending upon reaction temperature, usually several minutes to about 24 hours being enough to attain the purpose.

For reduction of the Schiff's base formed are used advantageously various metal hydride complex reducing agents including alkali metal borohydrides such as sodium borohydride, potassium borohydride, lithium borohydride, and sodium methoxyborohydride, alkali metal cyanoborohydrides such as sodium cyanoborohydride, alkali metal aluminum hydrides such as lithium aluminum hydride, and dialkylamine boranes such as dimethylamine borane. When sodium cyanoborohydride is used, the reaction is preferably conducted under acidic condition, for example in the presence of hydrochloric acid, acetic acid or the like.

The reaction temperature of this reduction varies depending on the Schiff's base and the reducing agent used, being usually 0° C.–40° C., occasionally, particularly in the initial stage of the reaction, the reaction is conducted under cooling to about 0° C.−−20° C. or by heating to about 100° C. The reaction time also varies depending upon the reaction temperature, Schiff's base to be reduced, and the reducing agent, usually several minutes to about 24 hours being enough to attain the purpose.

Reduction of the Schiff's base formed may be effected by means of catalytic reduction. That is, reduction can be effected by shaking or stirring the Schiff's base in an appropriate solvent in the presence of a catalyst for catalytic reduction in a stream of hydrogen. Catalysts for catalytic reduction include platinum black, platinum dioxide, palladium black, palladium carbon, and Raney nickel. Solvents used usually include water; alcohols such as methanol and ethanol; ethers such as dioxane and tetrahydrofuran, and N,N-dimethylformamide, which are used separately or in combination. The reaction is carried out usually at 0° C.–40° C. at atmospheric pressure, but may be carried out by applying pressure or by heating.

Desulfurization of the sulfur compound represented by the general formulas (6") and (8") in Processes 6" and 8" can be effected usually by allowing Raney nickel which is previously saturated with hydrogen to suspend in the solution of the sulfur compound, and then by shaking or by stirring. Usually a large excess (10 times (w/w) or more) of Raney nickel is used as compared to the amount of the sulfur compound. The solvents used include water, alcohols such as methanol, ethanol, propanol, butanol, and ethylene glycol, ethers such as methyl cellosolve, dioxane and tetrahydrofuran, ketones such as acetone and methyl ethyl ketone, aromatic hydrocarbons such as benzene and toluene, esters such as ethyl acetate, amides such as N,N-dimethylformamide, and solvents which affect no adverse effect on the reaction, and these solvents are used separately or in combination, and methanol and ethanol are used preferably. The reaction temperature is selected in the range of 0° C. to 150° C., and usually the reaction is conducted at room temperature or at the boiling point of the solvent by refluxing. The reaction time varies depending upon the kind of Raney nickel used and the reaction temperature, being usually about 0 minutes to about 24 hours.

The compounds (5"), (6"), and (8") are all novel pseudosugar derivatives having bis(methylthio) group or 1,3-dithian-2-spiro substituent, and important as the intermediates for production of the desired useful compounds (7") and (9"), namely the compound [II].

An inosose derivative represented by the general formula:

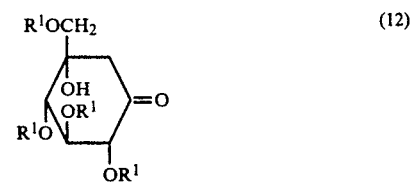

(12)

wherein $R^1$ is a protective group for hydroxyl, is also important as the intermediate for the preparation of valiolamine and its derivatives, and can be produced from the compound (5') by reductive dehalogenation or from the compound (5") by reductive desulfurization. The reductive dehalogenation of the compound (5') and the reductive desulfurization of the compound (5") have to be conducted under the condition which does not give rise to reduction of the carbonyl group. The dehalogenation is preferably carried out by using organic tin hydrides such as $(n-C_4H_9)_3SnH$ in aromatic organic solvents such as benzene and toluene, or by catalytic reduction in the presence of the catalyst such as palladium on barium sulfate and Lindlar catalyst in an appropriate solvent including alcohols such as methanol and ethanol, and ethers such as tetrahydrofuran and dioxane, and the desulfurization is preferably carried out by using Raney nickel in nonpolar solvents such as dioxane, tetrahydrofuran, benzene, toluene and ethyl acetate.

Halogens represented by X, $X^1$ and $X^2$ in the general formulas [I] and [I'] as well as FIG. 1 and 2 include chlorine and bromine.

Lower alkyl groups represented by $Q^1$ and $Q^2$ in the general formulas [I] and [I"] as well as FIG. 3 and 4 are independently lower alkyl groups having 1 to 3 carbon atoms, such as methyl, ethyl, propyl, and isopropyl, and the lower alkylene groups formed together by $Q^1$ and $Q^2$ include lower alkylene groups having 2 or 3 carbon atoms, such as ethylene and trimethylene.

The protective groups for hydroxyl represented by $R^1$ and $R^3$ in the general formulas [I], [I'], [I''], and [II] and FIGS. 1 to 4 include those used as hydroxyl-protective groups in chemistry of saccharides, such as ether type protective groups, acetal type protective groups, ketal type protective groups, ortho-ester type protective groups and occasionally acyl type protective groups.

Ether type protective groups used include lower alkyl groups having 1 to 5 carbon atoms which may be substituted by halogen, lower alkoxy group having 1 to 5 carbon atoms, benzyloxy group, or phenyl group; alkenyl groups having 2 to 4 carbon atoms; tri-substituted silyl groups of which substituents are lower alkyl groups having 1 to 5 carbon atoms, phenyl groups, benzyl groups and the like; benzyl groups which may be substituted by lower alkoxy group having 1 to 5 carbon atoms, or nitro group; lower alkoxy groups having 1 to 5 carbon atoms; and tetrahydropyranyl groups which may be substituted by halogen The halogens described above include fluorine, chlorine, bromine and iodine; the alkyl groups having 1 to 5 carbon atoms include methyl, ethyl, propyl, isopropyl, butyl, isobutyl, sec-butyl, tert-butyl, pentyl, isopentyl, and neopentyl; the alkoxy groups having 1 to 5 carbon atoms include methoxy, ethoxy, propoxy, butoxy, pentyloxy, vinyloxy, and allyloxy which may be substituted by halogen; the alkenyl groups having 2 to 4 carbon atoms include vinyl, allyl, isopropenyl, 1-propenyl, 1-butenyl, 2-butenyl, and 3-butenyl.

Ether type protective groups, in more concrete, are methyl, methoxymethyl, benzyloxymethyl, tert-butoxymethyl, 2-methoxyethoxymethyl, 2,2,2-trichloromethoxymethyl, ethyl, 1-ethoxyethyl, 1-methyl-1-methoxyethyl, 2,2,2-trichloroethyl, propyl, isopropyl, butyl, isobutyl, secbutyl, tert-butyl, ethoxyethyl, triphenylmethyl, p-methoxyphenyldiphenylmethyl; allyl; trimethylsilyl, tert-butyldimethylsilyl, tert-butyldiphenylsilyl; benzyl, p-methoxybenzyl, p-nitrobenzyl, p-chlorobenzyl; tetrahydropyranyl, 3-bromotetrahydropyranyl, 4-methoxytetrahydropyranyl, and tetrahydrofuranyl.

As acetal type, ketal type and ortho-ester type protective groups, are used advantageously those having 1 to 10 carbon atoms The examples are methylene, ethylidene, 1-tert- butylethylidene, 1-phenylethylidene, 2,2,2-trichloroethylidene; isopropylidene, butylidene, cyclopentylidene, cyclohexylidene, cycloheptylidene; benzylidene, p-methoxybenzylidene, 2,4-dimethoxybenzylidene, p-dimethylaminobenxzylidene, o-nitrobenzylidene; methoxymethylene, ethoxymethylene, dimethoxymethylene, 1-methoxyethylidene, and 1,2-dimethoxyethylidene.

Acyl type protective groups used include alkanoyl groups having 1 to 5 carbon atoms which may be substituted by halogen, alkoxy group having 1 to 5 carbon atoms, or phenoxy group which may have halogen, benzoyl groups which may be substituted by nitro group, phenyl group or lower alkyl group having 1 to 5 carbon atoms which may be substituted by halogen, benzoyl groups which may be substituted by lower alkoxycarbonyl group having 2 to 6 carbon atoms, alkoxycarbonyl groups having 2 to 6 carbon atoms which may be substituted by halogen, alkenyloxycarbonyl groups having 3 to 5 carbon atoms, benzyloxycarbonyl groups which may be substituted by lower alkoxy group having 1 to 5 carbon atoms or nitro group, and phenoxycarbonyl groups substituted by nitro group.

The halogens, lower alkyl groups having 1 to 5 carbon atoms, lower alkoxy groups having 1 to 5 carbon atoms, and alkenyl groups having 2 to 4 carbon atoms described above are the same as those given for ether type protective groups.

Acyl type protective groups, in more concrete, are formyl, acetyl, chloroacetyl, dichloroacetyl trichloroacetyl, trifluoroacetyl, methoxyacetyl, triphenylmethoxyacetyl, phenoxyacetyl, p-chlorophenoxyacetyl, propionyl, isopropionyl, 3-phenylpropionyl, isobutyryl, pivaloyl; benzoyl, p-nitrobenzoyl, p-phenylbenzoyl, o-(dibromomethyl)benzoyl, o-(methoxycarbonyl)benzoyl, 2,4,6-trimethylbenzoyl; methoxycarbonyl, ethoxycarbonyl, 2,2,2-trichloroethoxycarbonyl, isobutyloxycarbonyl; vinyloxycarbonyl, allyloxycarbonyl; benzyloxycarbonyl, p-methoxybenzyloxycarbonyl, 3,4-dimethoxybenzyloxycarbonyl, p-nitrobenzyloxycarbonyl; and p-nitrophenoxycarbonyl.

In addition, stannoxane type protective groups such as dibutylstannyl and tributylstannyl, cyclic carbonate type protective groups, and cyclic boronate type protective groups are used similarly for some classes of compound.

The kinds of the hydroxyl protective groups represented by $R^1$ and $R^3$ in the compound may be all the same or different from each other. Two hydroxyl groups may be protected with a single protective group, as when cyclic acetal type, cyclic ketal type, cyclic ortho-ester type, cyclic carbonate type, cyclic boronate type, and stannoxane type protective groups are used.

Representative amine residues represented by R2 in the general formula $R^2$—$NH_2$ are acyclic or cyclic hydrocarbons having 1 to 7 carbon atoms which may have a hydroxyl group which may be protected and/or phenyl group which may be substituted.

Such primary amines represented by the general formula $R^2$—$NH_2$ include acyclic alkylamines which may have a hydroxyl group and/or phenyl group which may be substituted, such as ethanolamine, 3-amino-1-propanol, 2-amino-1-propanol, 2-amino-1,3-propanediol, 1-amino-2-propanol, 2-amino-3-hydroxy-1-butanol, tris(hydroxymethyl)aminomethane, 2-amino-2-methyl-1,3-propanediol, 2-amino-2-methyl-1-propanol, 2-amino-3-methyl-1-butanol, 3-amino-1,2-propanediol, 4-amino-1,2-butanediol, 2-amino-1-butanol, 2-amino-1,4-butanediol, 2-amino-1,5-pentanediol, 5-amino-1-pentanol, 6-amino-1-hexanol, methylamine, ethylamine, propylamine, butylamine, benzylamine, phenethylamine, aminodiphenylmethane, 2-amino-1-phenylethanol, 2-amino-2-phenylethanol, 2-amino-3-phenyl-1-propanol, 2-amino-3-hydroxy-3-ehenyl-1-propanol, 2-amino-3-(4-hydroxyphenyl)-1-propanol, and β-amino-α-methylphenethylalcohol, amino-deoxy-alditols such as 1-amino-1-deoxy-D-glucitol, 2-amino-2-deoxy-D-glucitol, 1-amino-1-deoxy-D-mannitol, 2-amino-2-deoxy-D-galactitol, 1-amino-1-deoxy-D-ribitol, and 4-amino-4-deoxy-D-erythritol, cyclic alkylamines which may be substituted by hydroxyl group and/or phenyl group such as trans-2-aminocyclohexan-1-ol, trans-3-aminocyclohexan-1-ol, cis-3-aminocyclohexan-1-ol, trans-2-amino-1-phenylcyclohexan-1ol, cis-2-amino-1-phenylcyclohexan-1-ol, cyclohexylamine, cyclopentylamine, 1-amino-1-cyclopentanemethanol, and 2-aminocyclopentanol, inosamines such as myo-inosamine-1, myo-inosamine-2, myo-inosamine-4, neoinosamine-2, epi-inosamine-2, muco-inosamine-3, and scyllo-inosamine, C-(aminomethyl)inositols such as 2-aminomethyl-myo-inositol, diaminocyclitols such as streptamine, deoxystreptamine, fotamine, sporamine, and istamine, and pseudoaminosugars such as valienamine, validamine, hydroxyvalidamine, valiolamine, and 2-hydroxy-4-(hydroxymethyl)cyclopentylamine. The hydroxyl groups of the compounds described above may be protected. Examples of the amine residues represented by A include all of the amine residues (i.e. $R^2$) of the amines given as examples as the primary amines represented by $R^2$—$NH_2$ described above.

Examples of "hydroxyl groups which may be protected" represented by $R^2$ and Z include hydroxy, lower alkoxy having 1 to 4 carbon atoms such as methoxy, ethoxy, and trityloxy, and aralkyloxy groups such as benzyloxy In the general formula [II], the compound wherein A is a hydrogen atom, i.e. the compound (9') and (7"), can be produced also by subjecting a compound (11') and (9") wherein A moiety is a group which may also be used generally as an amino-protective group, such as benzyl group, p-methoxybenzyl group, 3,4-dimethoxybenzyl group, and di(p-methoxyphenyl)methyl group, to a reaction which is generally used for removal of amino-protective group, such as hydrogenolysis by catalytic reduction, a reaction with metallic sodium in liquid ammonia, and a reaction with an acid (e.g. concentrated sulfuric acid-trifluoroacetic acid, acetic acid, trifluoroacetic anhydride, formic acid).

When the compound [II] has a protected hydroxyl group, removal of the hydroxyl protective group can be effected by a per se known method. Acetal type protective groups such as cyclohexylidene group, isopropylidene group and benzylidene group, and ether type protective groups which can be removed by acid, such as trityl group and tetrahydropyranyl group, can be removed by hydrolysis with an acid such as hydrochloric acid, acetic acid, trifluoroacetic acid, p-toluenesulfonic acid, and sulfonate form ion exchange resin; acyl type protective groups such as acetyl group and benzoyl group can be removed by hydrolysis with an alkali such as ammonia, sodium hydroxide, barium hydroxide, and sodium methoxide; and benzyl ether type protective groups such as benzyl group and p-methoxybenzyl group can be removed by hydrogenolysis by catalytic reduction or reductive cleavage with metallic sodium in liquid ammonia.

The compounds including the pseudosugar derivatives (5'), (6'), (7'), (8'), (10'), (5"), (6"), and (8") can be isolated and purified by the per se known methods, such as concentration, concentration under reduced pressure, filtration, centrifugation, drying, freeze drying, absorption, desorption, and methods taking advantage of the difference in solubility in various solvents (e.g. extraction with solvent, partition, precipitation, crystallization, recrystallization), and chromatography (e.g. chromatography using ion exchange resin, active carbon, high porous polymer, Sephadex, Sephadex ion exchanger, cellulose, ion exchange cellulose, silica gel, or alumina).

Valiolamine and the N-substituted derivatives thereof, particularly N-substituted derivatives of valiolamine such as N-[2-hydroxy-1-(hydroxymethyl)ethyl]valiolamine, because of their potent α-glucosidase inhibiting activity to suppress the metabolism of carbohydrates, may prevent elevation of blood sugar level, being useful compounds for treatment and prevention of symptoms of hyperglycemia and various diseases due to hyperglycemia such as diabetes, obesity, and hyperlipemia.

The pseudosugar derivatives [I] of this invention are important as the starting substances for production of valiolamine and the N-substituted derivatives thereof as described above, and can be produced from D-glucose or D-glucono-δ-lactone which can be produced inexpensively and easily from D-glucose, via 1-C-(dihalomethyl)-D-glucopyranose derivative (2'), 1-C-[bis((low alkyl)thio)methyl]-D-glucopyranose derivative (2"), or 1-C-(1,3-dithian-2-yl)-D-glucopyranose derivative (2").

The compound [I] is useful for production of valiolamine and the N-substituted derivatives thereof, and particularly when, in synthesis of N-substituted valiolamine derivatives, the starting compound to constitute the N-substituent is easily available as an amino compound, the desired product can be synthesized more easily by using the compound [I] as the intermediate than by using valiolamine.

In the following, this invention is illustrated in more concrete with Reference Examples and Examples, but the invention is not limited only to these Examples. In the following examples, ratios for mixtures of solvents are expressed by volume (v/v), unless otherwise noted. $^1$H-NMR spectra were recorded, with tetramethylsilane ($Me_4Si$) as the external standard in $D_2O$ and as the internal standard in $CDCl_3$, with a Varian XL-100A spectrometer (100 MHz) and/or a Bruker AC-300 spectrometer (300 MHz).

REFERENCE EXAMPLE 1

2,3,4,6-Tetra-O-benzyl-1-C-(1,3-dithian-2-yl)-D-glucopyranose [i.e. 3,4,5,7-tetra-O-benzyl-D-gluco-2-heptosulose-(2,6) 1,1-(trimethylene dithioacetal)]

1,3-Dithiane (2.4 g) was dissolved in tetrahydrofuran (60 mL), to which a solution of n-butyllithium in n-hexane (1.6 M solution, 12.5 mL) was added dropwise in a stream of argon under cooling at $-60°$ — $-70°$ C., and then stirred at $-20°$ — $-30°$ C. for 2.5 hours. The mixture was cooled again to $-70°$ — $-75°$ C., to which a solution of 2,3,4,6-tetra-O-benzyl-D-glucono-δ-lactone (5.4 g) in tetrahydrofuran (15 mL) was added dropwise, and stirred at the same temperature for 1 hour. To the mixture 10%(w/v) ammonium chloride solution (100 mL) was added and the resulting oily substances were extracted with ethyl acetate (300 mL). The ethyl acetate extract was washed with 2N hydrochloric acid and saturated sodium hydrogencarbonate solution, dried over anhydrous sodium sulfate, and evaporated under reduced pressure. The residue was chromatographed on a column of silica gel (250 mL), washed with toluene, and eluted with toluene-ethyl acetate (15:1). The eluate was evaporated to dryness under reduced pressure to give a colorless syrup of 2,3,4,6-tetra-O-benzyl-1-C-(1,3-dithian-2-yl)-D-glucopyranose (6.3 g).

IR ($CHCl_3$): 3452 $cm^{-1}$; no absorption in C=O region (1700-1800 $cm^{-1}$); $[\alpha]^{26}_D$ +4.4° (c=1, $CHCl_3$); NMR ($CDCl_3$) δ: 1.82-2.06 (2H, m, —$SCH_2CH_2$—), 2.22-2.36 (2H, m, —$SCH_{ax}CH_2$—x 2), 3.30-3.47 (2H, m, —$SCH_{eq}CH_2$—x 2), 3.62 (1H, dd, J=2.2 Hz, 10.3 Hz) and 3.68 (1H, dd, J=4.3 Hz, 10.3 Hz)(6—$CH_2$), 3.63 (1H, d, J=1.6 Hz, —SCHS—), 3.68 (1H, t*, J=9.3 Hz, 9.9 Hz, 4—CH), 4.06 (1H, ddd, J=2.2 Hz, 4.3 Hz, 9.9 Hz, 5—CH), 4.11 (1H, t, J=9.2 Hz, 3—CH), 4.31 (1H, dd, J=1.6 Hz, 9.2 Hz, 2—CH), 4.32 (1H, s, —OH);

4.48 (2H, s), 4.60 (1H, d, J=11.0 Hz), 4.67 (1H, d, J=11.3 Hz), 4.88 (1H, d, J=11.0 Hz), 4.92 (1H, d, J=11.3 Hz) and 4.94 (2H, s)(PhCH$_2$—x 4); 7.18–7.36 (20H, m, C$_6$H$_5$—x 4)(* apparent splitting pattern).

Elemental analysis for C$_{38}$H$_{42}$O$_8$S$_2$:
Calc.(%): C, 60.27; H, 6.43; S, 9.73.
Found(%): C, 69.67; H, 6.43; S, 9.61.

REFERENCE EXAMPLE 2

2,3,4,6-Tetra-O-benzyl-1-C-(1,3-dithian-2-yl)-D-glucitol 2,3,4,6-Tetra-O-benzyl-1-C-(1,3-dithian-2-yl)-D-glucopyranose (9.76 g) was dissolved in tetrahydrofuran-ethyl ether (11:4, 150 mL), to which lithium aluminum hydride (2.4 g) was added in small portions under cooling with ice-water, and stirred at the same temperature for 3.5 hours. Methanol (10 mL) was added dropwise to the mixture and then evaporated under reduced pressure, and the residue was partitioned between ethyl acetate (250 mL) and 2N hydrochloric acid (200 mL). The aqueous layer was extracted further with ethyl acetate (250 mL), and the ethyl acetate extracts were combined, washed with saturated sodium hydrogencarbonate solution, dried over anhydrous sodium sulfate, and evaporated under reduced pressure. The residue was chromatographed on a column of silica gel (550 mL). The column was eluted with toluene-ethyl acetate (9:1) and then with toluene-ethyl acetate (5:1) to resolve the two stereoisomers ((1R)- and (1S)-isomers) of 2,3,4,6-tetra-O-benzyl-1-C-(1,3-dithian-2-yl)-D-glucitol. The fraction eluted with toluene-ethyl acetate (9:1) was evaporated to dryness under reduced pressure to give a colorless syrup (5.44 g) of the isomer showing [α]$^{26}_D$ −9.5° (c=1, CHCl$_3$), and the fraction eluted with toluene-ethyl acetate (5:1) was evaporated to dryness under reduced pressure to give a colorless syrup (1.14 g) showing [α]$^{26}_D$ −5.7° (c=1, CHCl$_3$).

The isomer eluted earlier:

[α]$^{26}_D$ −9.5° (c=1, CHCl$_3$); NMR (CDCl$_3$) δ:1.86–2.17 (2H, m, —SCH$_2$CH$_2$—), 2.67 (1H, ddd, J=2.8 Hz, 10.0 Hz, 13.3 Hz) and 2.77 (1H, ddd, J=2.8 Hz, 10.1 Hz, 13.0 Hz)(—SCH$\overline{\text{ax}}$CH$_2$—x 2), 2.86 (1H, d, J=5.2 Hz, 5—OH), 2.93–3.05 (2H, m, —SCH$\overline{\text{eq}}$CH$_2$—x 2), 3.55 (1H, dd, J=1.1Hz, 2.9 Hz, 1—OH), 3.60 (1H, dd, J=4.2 Hz, 9.8 Hz) and 3.64 (1H, dd, J=6.9 Hz, 9.8 Hz)(6—CH$_2$), 3.93 (1H, dd, J=3.2 Hz, 6.1 Hz, 4—CH), 3.99 (1H, t*, J=3.2 Hz, 4.1 Hz, 3—CH), 4.01–4.03 (2H, m, 1—CH, 5—CH), 4.16–4.22 (2H, m, 2—CH, —SCHS—); 4.51 (1H, d, J=11.8 Hz), 4.55 (1H, d, J=11.8 Hz), 4.58 (1H, d, J=11.2 Hz), 4.58 (2H, s), 4.61 (2H, s) and 4.67 (1H, d, J=11.2 Hz)(PhCH$_2$—x 4); 7.26–7.38 (20H, m, C$_6$H$_5$—x 4)(* apparent splitting pattern).

Elemental analysis for C$_{38}$H$_{44}$O$_6$S$_2$:
Calc.(%): C, 69.06; H, 6.71; S, 9.70.
Found(%) C, 69.56; H, 6.85; S, 9.39.

The isomer eluted later:

[α]$^{26}_D$ −5.7° (c=1, CHCl$_3$); NMR (CDCl$_3$) δ:1.82–2.05 (2H, m, —SCH$_2$CH$_2$—), 2.41–2.61 (2H, m, —SCH$\overline{\text{ax}}$CH$_2$—x 2), 2.66–2.83 (2H, m, —SCH$\overline{\text{eq}}$CH$_2$—x 2), 2.86 (1H, d, J=6.0 Hz, 1—OH), 2.95 (1H, d, J=5.2 Hz, 5—OH), 3.63 (1H, dd, J=5.1 Hz, 11.3 Hz) and 3.67 (1H, dd, J=3.9 Hz, 11.3 Hz)(6-CH$_2$), 3.76 (1H, dd, J=3.1 Hz, 7.2 Hz, 4—CH), 3.78 (1H, d, J=8.9 Hz, —SCHS—), 4.00 (1H, ddd, J=1.5 Hz, 6.0 Hz, 8.9 Hz, 1—CH), 4.08–4.16 (1H, m, 5—CH), 4.18 (1H, dd, J=3.1 Hz, 8.3 Hz, 3—CH), 4.38 (1H, dd, J=1.5 Hz, 8.3 Hz, 2—CH); 4.51 (1H, d, J=11.9 Hz), 4.56 (1H, d, J=11.9 Hz), 4.58 (1H, d, J=11.1 Hz), 4.63 (1H, d, J=11 1 Hz), 4.67 (1H, d, J=11.3 Hz), 4.70 (1H, d, J=11.3 Hz), 4.82 (1H, d, J=11.3 Hz) and 4.91 (1H, d, J=11 3 Hz)(PhCH$_2$—x 4); 7.25–7.35 (20H, m, C$_6$H$_5$—x 4).

Elemental analysis for C$_{38}$H$_{44}$O$_6$S$_2$:
Calc.(%): C, 69.06; H, 6.71; S, 9.70.
Found(%): C, 69.29; H, 6.86; S, 9.20.

REFERENCE EXAMPLE 3

2,3,4,6-Tetra-O-(tetrahydropyranyl)-1-C-(1,3-dithian-2-yl)-D-glucopyranose [i.e. 3,4,5,7-tetra-O-(tetrahydropyranyl)-D-gluco-2-heptosulose-(2,6) 1,1-(trimethylene dithioacetal)]

A solution of n-butyllithium in n-hexane (1.6 M solution, 25 mL) was added to a solution of 1,3-dithiane (4.8 g) in tetrahydrofuran (100 mL) in a stream of argon under cooling at −65°–−70° C., and stirred at −20°–−30° C. for 2.5 hours. The reaction mixture was cooled again to −70°–−7520 C., to which a solution of 2,3,4,6-tetra-O-(tetrahydropyranyl)-D-glucono-δ-lactone (10.3 g) in tetrahydrofuran (40 mL) was added dropwise, and stirred at the same temperature for 1 hour The reaction mixture was added to an ice-cooled 10%(w/v) ammonium chloride solution (300 mL), and the resulting oily substances were extracted with ethyl acetate (300 mL×2). The ethyl acetate extract was washed with water, 2N hydrochloric acid, and saturated sodium hydrogencarbonate solution, dried over anhydrous sodium sulfate, and evaporated under reduced pressure. The residue was chromatographed on a column of silica gel (500 mL). The column was washed with toluene-ethyl acetate (9:1), and eluted with toluene-ethyl acetate (4:1). The eluate was evaporated to dryness under reduced pressure to give a white powder (10.7 g) of 2,3,4,6-tetra-O-(tetrahydropyranyl)-1-C-(1,3-dithian-2-yl)-D-glucopyranose.

IR (KBr):3448 cm$^{-1}$; no absorption in C=O region (1700–1800 cm$^{-1}$).

Elemental analysis for C$_{30}$H$_{50}$O$_{10}$S$_2$:
Calc.(%): C, 56.76; H, 7.94; S, 10.10.
Found(%): C, 57.17; H, 7.90; S, 9.83.

REFERENCE EXAMPLE 4

2,3,4,6-Tetra-O-(tetrahydropyranyl)-1-C-(1,3-dithian-2-yl)-D-glucitol

Lithium aluminum hydride (1.74 g) was added in small portions under ice-cooling to a solution of 2,3,4,6-tetra-O-(tetrahydropyranyl)-1-C-(1,3-dithian-2-yl)-D-glucopyranose (6.9 g) in tetrahydrofuran-ethyl ether (3:1, 100 mL), and stirred at the same temperature for 5 hours Methanol (10 mL) was added to the mixture to work up the reaction, and then evaporated under reduced pressure. To the residue were added ethyl acetate (100 mL) and 2N hydrochloric acid (80 mL), the insoluble substances were filtrated off. The organic layer was separated, washed with water and saturated sodium hydrogencarbonate solution, dried over anhydrous sodium sulfate, and evaporated under reduced pressure. The residue was chromatographed on a column of silica gel (400 mL). The column was washed with toluene (500 mL) and eluted with toluene-ethyl acetate (3:2) and then with toluene-ethyl acetate (1:2). The compounds supposed to be the two stereoisomers ((1R)- and (1S)-isomers) of 2,3,4,6-tetra-O-(tetrahydropyranyl)-1-C-(1,3-dithian-2-yl)-D-glucitol were eluted separately. The fraction eluted with toluene-ethyl acetate (3:2) was evaporated to dryness under reduced pressure to give a colorless syrup (3.45 g), and the fraction eluted with toluene-ethyl acetate (1:2) was evaporated to dryness under reduced pressure to give a colorless syrup (1.52 g). The isomer eluted with toluene-ethyl acetate (3:2):
Elemental analysis for $C_{30}H_{52}O_{10}S_2$:
Calc.(%): C, 56.58; H, 8.23; S, 10.07.
Found(%): C, 56.60; H, 8.25; S, 10.23.
The isomer eluted with toluene-ethyl acetate (1:2):
Elemental analysis for $C_{30}H_{52}O_{10}S_2$:
Calc.(%): C, 56.58; H, 8.23; S, 10.07.
Found(%): C, 56.93; H, 8.02; S, 9.73.

REFERENCE EXAMPLE 5

2,3,4,6-Tetra-O-benzyl-1-C-[bis(methylthio)methyl]-D-glucopyranose [namely, 3,4,5,7-tetra-O-benzyl-D-gluco-2-heptosulose-(2,6) 1,1-(dimethyl dithioacetal)]

A solution of n-butyllithium in n-hexane (1.6 M solution, 37.5 mL) was added dropwise to a solution of bis(methylthio)methane (6.13 mL) in tetrahydrofuran (150 mL) in a stream of argon under cooling at $-65°--75°$ C., and stirred at $-20°--30°$ C. for 2.5 hours. The reaction mixture was cooled again to $-65°--70°$ C., to which a solution of 2,3,4,6-tetra-O-benzyl-D-glucono-δ-lactone (16.2 g) in tetrahydrofuran (60 mL) was added dropwise, stirred at the same temperature for 1 hour, and added to an ice-cooled 10%(w/v) ammonium chloride solution (300 mL). The resulting oily substances were extracted with ethyl acetate (300 mL x 2). The extract was washed with 2N hydrochloric acid and saturated sodium hydrogencarbonate solution, dried over anhydrous sodium sulfate, and evaporated under reduced pressure Ethyl ether-petroleum ether (1:4, 500 mL) was added to the residue and the mixture was refrigerated overnight to give 2,3,4,6-tetra-O-benzyl-1-C-[bis(methylthio)methyl]-D-glycopyranose as white crystals (16.0 g).

mp 96°-97° C.; $[\alpha]^{25}_D -24.6°$ (C=1, CHCl₃); IR (KBr): 3394 cm$^{-1}$; no absorption in C=O region (1700-1800 cm$^{-1}$); NMR (CDCl₃) δ:1.99 (3H, s), 2.14 (3H, s), 3.45-4.20 (7H, m), 4.39 (1H, s), 4.50-5.07 (8H, m), 7.05-7.45 (20H, m); NMR (CDCl₃, 300MHz)δ:1.97 (3H, s, CH₃S—), 2.15 (3H, s, CH₃S—), 3.55 (1H, dd, J=1.7 Hz, 11.2 Hz) and 3.74 (1H, dd, J=4.4 Hz, 11.2 Hz)(6—CH₂), 3.64 (1H, dd, J=8.6 Hz, 9.9 Hz, 4—CH), 3.89 (1H, s, (MeS)₂CH—), 3.98 (1H, ddd, J=1.7 Hz, 4.4 Hz, 9.9 Hz, 5—CH), 4.10 (1H, t*, J=8.6 Hz, 9.4 Hz, 3—CH), 4.16 (1H, broad d, J=9.4 Hz, 2—CH), 4.44 (1H, broad s, —OH); 4.49 (1H, d, J=12.2 Hz), 4.60 (1H, d, J=12.2 Hz), 4.64 (1H, d, J=10.9 Hz), 4.76 (1H, d, J=11 5 Hz), 4.85 (1H, d, J=10 9 Hz), 4.92 (2H, s) and 5.00 (1H, d, J=11.5 Hz)(PhCH₂—x 4); 7.24-7.34 (20H, m, C₆H₅—x 4)(* apparent splitting pattern).
Elemental analysis for $C_{37}H_{42}O_6S_2$:
Calc.(%): C, 68.70; H, 6.54; S, 9.91.
Found(%): C, 68.61; H, 6.62; S, 9.64.

REFERENCE EXAMPLE 6

2,3,4,6-Tetra-O-benzyl-1-C-[bis(methylthio)methyl]-D-glucitol 2,3,4,6-Tetra-O-benzyl-1-C-[bis(methylthio)methyl]-D-glucopyranose (4 0 g) was dissolved in tetrahydrofuran (140 mL), to which lithium aluminum hydride (2.8 g) was added in portions under ice-cooling, and stirred at the same temperature for 18 hours and then at room temperature for 3 hours Methanol (50 mL) was added dropwise to the mixture under ice-cooling, and evaporated under reduced pressure. The residue was added to a mixture of ethyl acetate (200 mL) and water (200 mL) under ice-cooling, and acidified (pH 1) with 2N hydrochloric acid under stirring. The ethyl acetate layer was separated and the aqueous layer was extracted with ethyl acetate (200 mL). The ethyl acetate extracts were combined, washed with water and saturated sodium hydrogencarbonate solution, dried over anhydrous sodium sulfate, and evaporate under reduced pressure. The residue was chromatographed on a column of silica gel (500 mL) with toluene-ethyl acetate (6:1) to resolve the two isomers, i.e. (1R)- and (1S)-isomers of 2,3,4,6-tetra-O-benzyl-1-C-[bis(methylthio(methyl]-D-glucitol. The fraction eluted earlier (550–900 mL) was evaporated to dryness under reduced pressure, to give an isomer (11.5 g) showing $[\alpha]^{25}_D -5.8°$ (c=1, CHCl₃) as a colorless syrup, and the fraction eluted later (1.1–1.8 L) was evaporated to dryness under reduced pressure to give an isomer (0.9 g) showing $[\alpha]^{25}_D -12.7°$ (c=1, CHCl₃) as a colorless syrup.

The isomer eluted earlier:
NMR (CDCl₃)δ:2.12 (6H, s, CH₃S—x 2), 2.84 (1H, d, J=5.2 Hz, 5—OH), 3.44 (1H, dd, J=0.5 Hz, 2.6 Hz, 1—OH), 3.62 (2H, d, J=4.8 Hz, 6—CH₂), 3.85 (1H, dd, J=0.5 Hz, 2.7Hz, (MeS)₂CH—), 3.93 (1H, dd, J=3.5 Hz, 6.2 Hz, 4—CH), 4.03 (1H, t*, J=3.5 Hz, 4.2 Hz, 3—CH), 4.05-4.10 (1H, m, 5-CH), 4.15 (1H, dd, J=4.2 Hz, 8.3 Hz, 2—CH), 4,23 (1H, td*, J=2.6 Hz, 2.7 Hz, 8.3 Hz, 1—CH); 4.50 (1H, d, J=11.9 Hz), 4.55 (1H, d, J=11.9 Hz), 4.58 (1H, d, J=11.5 Hz), 4.60 (1H, d, J=11.2 Hz), 4.61 (1H, d, J=11.2 Hz), 4.63 (1H, d, J=11 5 Hz), 4.65 (1H, d, J=11.2 Hz) and 4.71 (1H, d, J=11.2 Hz)(PhCH₂—x 4); 7.24-7.38 (20H, m, C₆H₅—x 4)(* apparent splitting pattern).
Elemental analysis for $C_{37}H_{44}O_6S_2$:
Calc.(%): C, 68.49; H, 6.83; S, 9.88.
Found(%): C, 68.78; H, 6.92; S, 9.76.

The isomer eluted later:
NMR (CDCl₃)δ:1.97 (3H, s, CH₃S—), 1.99 (3H, s, CH₃S—), 2.96 (1H, d, J=5.2 Hz, —OH), 3.05 (1H, d, J=5.1 Hz, —OH), 3.58-3.69 (3H, m, 1—CH, 6—CH₂), 3.73 (1H, dd, J=3.0 Hz, 6.9 Hz, 4—CH), 3.80 (1H, d, J=9.1 Hz, (MeS)₂CH—), 4.08-4.15 (1H, m, 5—CH), 4.18 (1H, dd, J=3.0 Hz, 8.3 Hz, 3—CH), 4.37 (1H, dd, J=1.5 Hz, 8.3 Hz, 2—CH); 4.50 (1H, d, J=11.9 Hz), 4.55 (1H, d, J=11.9 Hz), 4.57 (1H, d, J=11.5 Hz), 4.61 (1H, d, J=11.5 Hz), 4.68 (1H, d, J=11.3 Hz), 4.73 (1H, d, J=11.4 Hz), 4.82(1H, d, J=11.3 Hz) and 4.94 (1H, d, J=11.4 Hz)(PhCH₂—x 4); 7.25-7.34 (20H, m, C₆H₅—x 4).
Elemental analysis for $C_{37}H_{44}O_6S_2$:
Calc.(%): C, 68.49; H, 6.83; S, 9.88.
Found(%): C, 68.82; H, 6.99; S, 9.58.

REFERENCE EXAMPLE 7

2,3,4,6-Tetra-O-benzyl-1-C-[bis(methylthio)methyl]-D-xylo-5-hexosulose

A solution of trifluoroacetic anhydride (3.2 mL) in dichloromethane (20 mL) was added dropwise to a solution of dimethyl sulfoxide (2.2 mL) in dichloromethane (25 mL) under cooling at $-65°--70°$ C., and stirred at the same temperature for 20 minutes. To the mixture was added dropwise a solution of a mixture of the (1R)- and (1S)-isomers of 2,3,4,6-tetra-O-benzyl-1-C-[bis(methylthio)methyl]-D-glucitol (3.2 g) in dichloromethane (20 mL) at $-65°--70°$ C., and stirred at the same temperature for 1 hour. A solution of triethylamine (5.8 mL) in dichloromethane (20 mL) was added dropwise to the mixture under cooling at the same temperature, and stirred for 15 minutes The cooling bath was removed and the mixture was stirred to warm to 0° C. The reaction mixture was added to a mixture of dichloromethane (100 mL) and ice-water (50 mL). The dichloromethane layer was separated, washed with 2N hydrochloric acid and saturated sodium hydrogencarbonate solution, dried over anhydrous sodium sulfate, and evaporated under reduced pressure The residue was chromatographed on a column of silica gel (250 mL). The column was washed with toluene and then eluted with toluene-ethyl acetate (9:1). The eluate was evaporated to dryness under reduced pressure to give 2,3,4,6-tetra-O-benzyl-1-C-[bis(methylthio)methyl]-D-xylo-5-hexosulose (2.9 g) as a colorless syrup.

$[\alpha]^{25}_D -33.9°$ (c=1, $CHCl_3$); IR($CHCl_3$): 1731 $cm^{-1}$.

Elemental analysis for $C_{37}H_{40}O_6S_2$:
Calc.(%): C, 68.92; H, 6.25; S, 9.95.
Found(%): C, 69.22; H, 6.23; S, 9.74.

REFERENCE EXAMPLE 8

2,3,4,6-Tetra-O-benzyl-1-C-[bis(methylthio)methyl]-D-xylo-5-hexosulose

A solution of trifluoroacetic anhydride (16 mL) in dichloromethane (57 mL) was added dropwise to a solution of dimethyl sulfoxide (12.2 mL) in dichloromethane (150 mL) at $-65°--70°$ C. with stirring and the stirring was continued for 20 minutes at the same temperature. To the mixture was added dropwise a solution of 2,3,4,6-tetra-O-benzyl-1-C-[bis(methylthio)-methyl]-D-glucitol (the isomer of $[\alpha]_D-5.8°$, 18.4 g) in dichloromethane (100 mL) with stirring, and then the mixture was stirred for 1 hour at $-65°--70°$ C. A solution of triethylamine (31.8 mL) in dichloromethane (100 mL) was added dropwise with stirring and then the stirring was continued for 15 minutes at $-65°--70°$ C. The cooling bath was removed and the mixture was stirred to warm to 0° C. The reaction mixture was added to a mixture of dichloromethane (240 mL) and ice-water (240 mL). The organic layer was separated and washed with 2N hydrochloric acid and saturated sodium hydrogencarbonate solution, dried over anhydrous sodium sulfate, and then evaporated to dryness under reduced pressure to give 2,3,4,6-tetra-O-benzyl-1-C-[bis(methylthio)methyl]-D-xylo-5-hexosulose (17.8 g) as a light yellow syrup.

IR ($CHCl_3$):1729, 1715 $cm^{-1}$; NMR ($CDCl_3$)δ:1.98 (3H, s, $CH_3S$—), 1.99 (3H, s, $CH_3S$—), 4.01 and 4.12 (each 1H, ABq, J=18.0 Hz, 6—$CH_2$), 4.13 (1H, dd, J=3.7 Hz, 4.9 Hz, 3—CH), 4.19 (1H, d, J=3.7 Hz, 4—CH); 4.27 (1H, d, J=12.2 Hz), 4.31 (1H, d, J=12.2 Hz), 4.38 (1H, d, J=11.6 Hz), 4.43 (1H, d, J=11.0 Hz), 4.49 (1H, d, J=11.2 Hz), 4.55 (1H, d, J=11.6 Hz), 4.62 (1H, d, J=11.0 Hz) and 4.74 (1H, d, J=11.2 Hz)($PhCH_2$—x 4); 4.72 (1H, d, J=4.9 Hz, 2—CH), 4.97 (1H, s, $(MeS)_2CH$—), 7.15-7.37 (20H, m, $C_6H_5$—x 4).

REFERENCE EXAMPLE 9

2,3,4,6-Tetra-O-benzyl-1-C-(dichloromethyl)-D-glucopyranose

To a solution of diisopropylamine (4.2 mL) in tetrahydrofuran (30 mL), a solution of n-butyllithium in n-hexane (1.6 M solution, 18.8 mL) was added dropwise in a stream of argon at $-5°--10°$ C. and stirred at the same temperature for 1 hour. The solution was added dropwise to a solution of 2,3,4,6-tetra-O-benzyl-D-glucono-δ-lactone (5.4 g) in dichloromethane (20 mL) in a stream of argon at $-70°--75°$ C. and stirred at the same temperature for 1 hour. The reaction mixture was added to a mixture of dichloromethane (200 mL) and 2N hydrochloric acid (100 mL) for partition. The organic layer was separated, washed with water and saturated sodium hydrogencarbonate solution, dried over anhydrous sodium sulfate, and evaporate under reduced pressure. The residue was chromatographed on a column of silica gel (400 mL) with toluene-ethyl acetate (20:1). The eluate was evaporated under reduced pressure. Petroleum ether (100 mL) was added to the residue and refrigerated overnight to give 2,3,4,6-tetra-O-benzyl-1-C-(dichloromethyl)-D-glucopyranose as white crystals (5.9 g).

mp 72°-73° C.; $[\alpha]^{23}_D +20.2°$ (c=1, $CHCl_3$); IR (KBr): 3402 $cm^{-1}$; no absorption in C=O region (1700-1800 $cm^{-1}$); NMR ($CDCl_3$)δ:3.29 (1H, d, J=1.1 Hz, —OH), 3.73 (1H, dd, J=1.8 Hz, 11.6 Hz) and 3.84 (1H, dd, J=3.9 Hz, 11.6 Hz)(6—$CH_2$), 3.75 (1H, dd, J=8.9 Hz, 9.8 Hz, 4—CH), 3.99 (1H, ddd, J=1.8 Hz, 3.9 Hz, 9.8 Hz, 5—CH), 4.00 (1H, dd, J=1.1 Hz, 8.9 Hz, 2—CH), 4.07 (1H, t, J=8.9 Hz, 3—CH); 4.61 (1H, d, J=12.3 Hz), 4.67 (1H, d, J=11.1 Hz), 4.71 (1H, d, J=12.3 Hz), 4.71 (1H, d, J=11.0 Hz), 4.85 (1H, d, J=10.9 Hz), 4.88 (1H, d, J=11.0 Hz), 4.96 (1H, d, J=10.9 Hz) and 4.97 (1H, d, J=11.1 Hz)($PhCH_2$—x 4); 5.81 (1H, s, —$CHCl_2$), 7.21 -7.40 (20H, m, $C_6H_5$—x 4).

Elemental analysis for $C_{35}H_{36}Cl_2O_6$:
Calc.(%): C, 67.42; H, 5.82; Cl, 11.37.
Found(%): C, 67.81; H, 5.80; Cl, 11.62.

REFERENCE EXAMPLE 10

2,3,4,6-Tetra-O-benzyl-1-C-(dichloromethyl)-D-glucitol (a) To a solution of 2,3,4,6-tetra-O-benzyl-1-C-(dichloromethyl)-D-glucopyranose (1.0 g) in tetrahydrofuran (100 mL), sodium borohydride (0.5 g) was added under cooling with ice-water, and stirred at the same temperature for 30 minutes and then at room temperature overnight. The mixture was evaporated under reduced pressure, and the residue was partitioned between ethyl acetate (60 mL) and water (30 mL). The organic layer was washed with 2N hydrochloric acid and saturated sodium hydrogencarbonate solution, dried over anhydrous sodium sulfate, and evaporated under reduced pressure. The residue was chromatographed on a column of silica gel (150 mL) with toluene-ethyl acetate (6:1). The eluate was evaporated to dryness under reduced pressure to give a mixture of the two isomers ((1R)- and (1S)-isomers) of 2,3,4,6-tetra-O-benzyl-1-C-(dichloromethyl)-D-glucitol (0.75 g) as a colorless syrup.

NMR ($CDCl_3+D_2O$)δ:3.62 (2H, d, J=4.5 Hz), 3.65-4.24 (5H, m), 4.38-4.82 (8H, m), 5.65 (d, J=6 Hz) and 5.95 (d, J=2 Hz) (total 1H), 7.25-7.4 (20H, m).

Elemental analysis for $C_{35}H_{38}Cl_2O_6$:
Calc.(%): C, 67.20; H, 6.12; Cl, 11.33.
Found(%) C, 67.52; H, 6.18; Cl, 11.32.

(b) To a solution of diisopropylamine (8.4 mL) in tetrahydrofuran (60 mL), a solution of n-butyllithium in n-hexane (1.6 M solution, 37.6 mL) was added dropwise in a stream of argon at $-10°--20°$ C. and stirred at the same temperature for 1 hour The mixture was added dropwise to a solution of 2,3,4,6-tetra-O-benzyl-D-glucono-δ-lactone (10.8 g) in dichloromethane (40 mL) in a stream of argon at $-70°--75°$ C. and stirred at the same temperature for 1 hour. The reaction mixture was added to a mixture of dichloromethane (200 mL) and 2N hydrochloric acid (200 mL) for partition. The organic layer was separated, washed with water and saturated sodium hydrogencarbonate solution, dried over anhydrous sodium sulfate, and evaporated under reduced pressure to give crude 2,3,4,6-tetra-O-benzyl-1-C-(dichloromethyl)-D-glucopyranose as a colorless syrup (12.5 g). This syrup (12.5 g) was dissolved in tetrahydrofuran (130 mL), to which sodium borohydride (6.6 g) was added under cooling with ice-water, and stirred at the same temperature for 30 minutes and then at room temperature overnight. The mixture was evaporated under reduced pressure, and the residue was partitioned between ethyl acetate (600 mL) and water (300 mL). The ethyl acetate layer was washed with 2N hydrochloric acid and saturated sodium hydrogencarbonate solution, dried over anhydrous sodium sulfate, and evaporated under reduced pressure. The residue was chromatographed on a column of silica gel (600 mL) with toluene-ethyl acetate (6:1). The eluate was evaporated to dryness under reduced pressure to give a mixture of (1R)- and (1S)-isomers of 2,3,4,6-tetra-O-benzyl-1-C-(dichloromethyl)-D-glucitol as a colorless syrup (10.6 g).

NMR (CDCl$_3$+D$_2$O, 300 MHz)$\delta$:3.63 (d, J=4.2 Hz) and 3.64 (d, J=4.5 Hz)(total 2H, 6—CH$_2$), 3.72 (dd, J=2.8 Hz, 7.1 Hz) and 3.91 (dd, J=3.7 Hz, 6.6 Hz)(total 1H, 4—CH), 3.80 (dd, J=4.5 Hz, 8.7 Hz) and 4.25 (dd, J=2.2 Hz, 7.8 Hz)(total 1H, 2—CH), 3.96 (dd, J=2.2 Hz, 6.8 Hz) and 4.17 (dd, J=1.9 Hz, 8.7 Hz)(total 1H, 1—CH), 4.00–4.15 (2H, m, 3—CH, 5—CH), 4.55–4.88 (8H, m, PhCH$_2$—x 4), 5.66 (d, J=6.8 Hz) and 5.98 (d, J=1.9 Hz)(total 1H, —CHCl$_2$), 7.22–7.38 (20H, m, C$_6$H$_5$—x 4).

Elemental Analysis for C$_{35}$H$_{38}$Cl$_2$O$_6$:
Calc.(%): C, 67.20; H, 6.12; Cl, 11.33.
Found(%): C, 67.46; H, 6.22; Cl, 11.31.

REFERENCE EXAMPLE 11

2,3,4,6-Tetra-O-benzyl-1-C-(dibromomethyl)-D-glucopyranose

To a solution of dicyclohexylamine (5.44 g) in tetrahydrofuran (30 mL) was added dropwise a solution of n-butyllithium in n-hexane (1.6 M solution, 19 mL) in a stream of argon at 0°–10° C. and stirred at the same temperature for 1 hour. The solution was added dropwise to a solution of 2,3,4,6-tetra-O-benzyl-D-glucono-$\delta$-lactone (5.4 g) and dibromomethane (2.5 mL) in tetrahydrofuran (30 mL) in a stream of argon at −70°–−75° C. and stirred at the same temperature for 1 hour. The reaction mixture was added to a mixture of ethyl acetate (200 mL) and 2N hydrochloric acid (100 mL) for partition. The organic layer was separated, and the aqueous layer was extracted further with ethyl acetate (100 mL). The organic layers were combined and washed with water and saturated sodium hydrogencarbonate solution, dried over anhydrous sodium sulfate, and evaporated under reduced pressure. The residue was chromatographed on a column of silica gel (400 mL) with toluene-ethyl acetate (20:1). The eluate was evaporated under reduced pressure. Ethyl ether-petroleum ether (1:7, 40 mL) was added to the residue and refrigerated overnight to give 2,3,4,6-tetra-O-benzyl-1-C-(dibromomethyl)-D-glucopyranose as white crystals (4.4 g).

mp 77°–78° C.; [α]$^{23}$$_D$+18.6° (c=1, CHCl$_3$); IR (KBr): 3364 cm$^{-1}$; no absorption in C=O region (1700-1800 cm$^{-1}$); NMR (CDCl$_3$)$\delta$:3.24 (1H, s), 3.6–4.2 (6H, m), 4.55–5.05 (8H, m), 5.78 (1H, s), 7.1–7.5 (20H, m).

Elemental analysis for C$_{35}$H$_{36}$Br$_2$O$_6$:
Calc.(%): C, 59.00; H, 5.09; Br, 22.43.
Found(%): C, 59.25; H, 4.95; Br, 22.44.

REFERENCE EXAMPLE 12

2,3,4,6-Tetra-O-benzyl-1-C-(dibromomethyl)-D-glucitol

To a solution of 2,3,4,6-tetra-O-benzyl-1-C-(dibromomethyl)-D-glucopyranose (3.15 g) in tetrahydrofuran (32 mL) was added sodium borohydride (1.6 g) under cooling with ice-water and the mixture was stirred at the same temperature for 1 hour and then at room temperature overnight. The mixture was evaporated under reduced pressure, and the residue was partitioned between ethyl acetate (150 mL) and water (50 mL). The organic layer was washed with 2N hydrochloric acid and saturated sodium hydrogencarbonate solution, dried over anhydrous sodium sulfate, and evaporated under reduced pressure. The residue was chromatographed on a (6:1). The eluate was evaporated to dryness under reduced pressure to give a mixture of (1R)- and (1S)- isomers of b 2,3,4,6-tetra-O-benzyl-1-C-(dibromomethyl)-D-glucitol (2.13 g) as a colorless syrup.

NMR (CDCl$_3$+D$_2$O)$\delta$:3.5–4.9 (15H, m), 5.68 (d, J=8 Hz) and 6.13 (d, J=3 Hz) (total 1H), 7.1–7.5 (20H, m).

Elemental analysis for C$_{35}$H$_{38}$Br$_2$O$_6$:
Calc.(%): C, 58.84; H, 5.36; Br, 22.37.
Found(%): C, 59.15; H, 5.23; Br, 21.94.

EXAMPLE 1

(1S)-(1(OH),2,4/1,3)-2,3,4-Tri-O-benzyl-1-C-(benzyloxymethyl)-5-oxo-6,6-(trimethylenedithio)-1, 2,3,4-cyclohexanetetrol Dimethyl sulfoxide (11.4 mL) was dissolved in dichloromethane (165 mL), to which a solution of trifluoroacetic anhydride (16.3 mL) in dichloromethane (65 mL) was added dropwise under cooling at −65°–−70° C., and stirred at the same temperature for 30 minutes. To the mixture, a solution of 2,3,4,6-tetra-O-benzyl-1-C-(1,3-dithian-2-yl)-D-glucitol (12.8g, the isomer of [α]$^{26}$$_D$−9.5° )in dichloromethane (85 mL) was added dropwise and stirred at −65°–−70° C. for 1 hour. To the mixture, a solution of triethylamine (21.5 mL) in dichloromethane (125 mL) was then the mixture was stirred for 15 minutes. The cooling bath was removed and the mixture was stirred to warm to 0° C. The reaction mixture was added to a mixture of dichloromethane (250 mL) and ice-water (350 mL), and the dichloromethane layer was separated. The organic layer was washed with 2N hydrochloric acid and saturated sodium hydrogencarbonate solution, dried over anhydrous sodium sulfate, and evaporated to dryness under reduced pressure to give a light yellow syrup of 2,3,4,6-tetra-O-benzyl-1-C-(1,3-dithian-2-yl)-D-xylo-5-hexosulose (12.4 g). The syrup was chromatographed on a column of silica gel (550 mL) with toluene-ethyl acetate (9:1). The eluate was evaporated under reduced pressure. Ethyl ether-petroleum ether (1:4, 350 mL) was added to the residue, and the mixture was refrigerated to give (1S)-(1(OH),2,4/1,3)-2,3,4-tri-O-benzyl-1-C-(benzyloxymethyl)-5-oxo-6,6-(trimethylenedithio)-1,2,3,4-cyclohexanetetrol (7.1 g) as white crystals.

mp 139–141° C.; [α]$^{26}$$_D$−57.3° b 26D -57.3° (c=1, CHCl$_3$); IR (KBr): 3432, 1728 cm$^{-1}$; NMR (CDCl$_3$)$\delta$:1.76–1.90 and 2.01–2.07 (each 1H, m, —SCH$_2$CH$_2$—), 2.41 (1H, ddd, J=2.3 Hz, 12.3 Hz, 14.2 Hz, —SCHax), 2.54–2.74 (2H, m, —SCHeq x 2), 2.99 (1H, s, —OH), 3.52 (1H, dt*, J=3.5 Hz, 13.5Hz, 13.9

Hz, —SCHax), 3.85 and 4.03 (each 1H, ABq, J=9.7 Hz, —CH$_2$—), 4.05 (1H, t*, J=9.3 Hz, 9.7 Hz, 3—CH), 4.41 (1H, d, J=9.3Hz, 2—CH); 4.56 (1H, d, J=11.8Hz), 4.67 (1H, d, J=11.4 Hz), 4.68 (1H, d, J=11.8 Hz), 4.73 (1H, d, J=10.7 Hz), 4.74 (1H, d, J=10.7 Hz), 4.94 (1H, d, J=10.7 Hz), 4.95 (1H, d, J=10.7 Hz) and 4.95 (1H, d, J=11.4 Hz)(PhCH$_2$—x 4); 5.27 (1H, d, J=9.7 Hz, 4—CH), 7.18–7.47 (20H, m, C$_6$H$_5$—x 4)(* apparent splitting pattern).

Elemental Analysis for C$_{38}$H$_{40}$O$_6$S$_2$:
Calc.(%): C, 69.48; H, 6.14; S, 9.76.
Found(%) C, 69.42; H, 6.26; S, 9.81.

EXAMPLE 2

(1S)-(1(OH),2,4/1,3)-2,3,4-Tri-O-benzyl-1-C-(benzyloxymethyl)-5-oxo-6,6-(trimethylenedithio)-1, 2,3,4-cyclohexanetetrol A solution of trifluoroacetic anhydride (3.2 mL) in dichloromethane (13 mL) was added dropwise to a solution of dimethyl sulfoxide (2.2 mL) in dichloromethane (35 mL) at −65°-−70° C. with stirring and then stirred for 30 minutes at the same temperature. To the mixture was added dropwise a solution of 2,3,4,6-tetra-O-benzyl-1-C-(1,3-dithian-2-yl)-D-glucitol (2.5 g, the isomer of $[\alpha]^{26}_D$ −5.7°) in dichloromethane with stirring, and the mixture was stirred for 1 hour at −65°-−70° C. A solution of triethylamine (4.2 mL) in dichloromethane (25 mL) was added dropwise to the mixture at −65°-−70° C. with stirring and then stirred for 15 minutes. The cooling bath was removed and the mixture was stirred to warm to 0° C. The mixture was distributed between dichloromethane (65 mL) and ice-water (65 mL). The organic layer was washed with 2N hydrochloric acid and saturated sodium hydrogencarbonate solution, dried over anhydrous sodium sulfate, and then evaporated under reduced pressure to give 2,3,4,6-tetra-O-benzyl-1-C-(1,3-dithian-2-yl)-D-xylo-5-hexosulose (2.5 g) as a light yellow syrup.

Sodium acetate (2.5 g) and 18-crown-6 (0.1 g) were added to a solution of the ketose derivative (2.5 g) in toluene (100 mL) and the mixture was stirred overnight at room temperature. The mixture was filtered off and the insoluble materials were washed with toluene (50 mL). The filtrate and the washings were combined and washed with 2N hydrochloric acid and saturated sodium hydrogencarbonate solution, dried over sodium sulfate, and then evaporated under reduced pressure Methanol (20 mL) was added to the residue, and the mixture was refrigerated overnight to give (1S)-(1(OH),2,4/1,3)-2,3,4-tri-O-benzyl-1-C-(benzyloxymethyl)-5-oxo-6,6-(trimethylenedithio)-1,2,3,4-cyclohexanetetrol (2.0 g) as white crystals.

Elemental analysis for C$_{38}$H$_{40}$O$_6$S$_2$:
Calc.(%): C, 49.83; H, 6.14; S, 9.76.
Found(%): C, 69.42; H, 6.26; S, 9.81.

EXAMPLE 3

(1S)-(1(OH),2,4/1,3)-2,3,4-Tri-O-benzyl-1-C-(benzyloxymethyl)-5-oxo-1,2,3,4-cyclohexanetetrol To a solution of (1S)-(1(OH),2,4/1,3)-2,3,4-tri-O-benzyl-1-C-(benzyloxymethyl)-5-oxo-6,6-(trimethylenedithio)-1,2,3,4-cyclohexanetetrol (1.1 g) in dioxane (30 mL) was added Raney nickel (3.0 g), and the mixture was heated at 80° C. for 1.5 hours with stirring. The insoluble materials were filtered off and washed with dioxane. The filtrate and the washings were combined and evaporated under reduced pressure. The residue was chromatographed on a column of silica gel (100 mL) with toluene-ethyl acetate (6:1). The eluate was evaporated under reduced pressure, and ethyl ether-petroleum ether (1:1, 10 mL) was added to the residue. The mixture was refrigerated overnight to give (1S)-(1(OH),2,4/1,3)-2,3,4-tri-O-benzyl-1-C-(benzyloxymethyl)5-oxo-1,2,3,4-cyclohexanetetrol as white crystals.

mp 84°–85° C.; $[\alpha]^{22}_D$+45.1 (c=1, CHCl$_3$); IR (KBr): 3440, 1735 cm$^{-1}$; NMR (CDCl$_3$) δ:2.39 (1H, d, J=2.0 Hz, —OH), 2.47 (1H, d, J=14.5 Hz, 6—CHeq), 2.84 (1H, ddd, J=0.9 Hz, 2.0 Hz, 14.5 Hz, 6—CHax), 3.15 and 3.53 (each 1H, ABq, J=8.6 Hz, —CH$_2$O—), 4.01 (1H, t, J=9.0 Hz, 3—CH), 4.06 (1H, d, J=9.0 Hz, 2—CH), 4.14 (1H, dd, J=0.9 Hz, 9.0 Hz, 4—CH); 4.41 (1H, d, J=11.8 Hz), 4.47 (1H, d, J=11.8 Hz), 4.55 (1H, d, J=10.7 Hz), 4.56 (1H, d, J=11.7 Hz), 4.75 (1H, d, J=10.7 Hz), 4.95 (1H, d, J=10.7 Hz), 4.96 (1H, d, J=11.7 Hz) and 4.99 (1H, d, J=10.7 Hz)(PhCH$_2$—x 4); 7.15–7.42 (20H, m, C$_6$H$_5$—x 4).

Elemental Analysis C$_{35}$H$_{36}$O$_6$:
Calc.(%): C, 76.06; H,6.57.
Found(%): C, 76.19; H,6.59.

EXAMPLE 4

(1S)-(1(OH),2,4,5/1,3)-5-Amino-1-C-(hydroxymethyl)-1,2,3,4-cyclohexanetetrol (valiolamine)

(1S)-(1(OH),2,4/1,3)-2,3,4-Tri-O-benzyl-1-C-(benzyloxymethyl)-5-oxo-6,6-(trimethylenedithio)-1,2,3,4-cyclohexanetetrol (600 mg) was dissolved in methanol (35 mL), to which hydroxylamine hydrochloride (720 mg) and sodium acetate (1.4 g) were added. The mixture was stirred at room temperature overnight and then heated under reflux for 2 hours. The mixture was evaporate under reduced pressure, and the residue was partitioned between ethyl acetate and water. The organic layer was washed with 2N hydrochloric acid and saturated sodium hydrogencarbonate solution, dried over anhydrous sodium sulfate, and evaporated under reduced pressure. A solution of the residue (420 mg) in methanol (10 mL) was added to a suspension of Raney nickel (15 g) in methanol (50 mL) which was previously stirred in a stream of hydrogen at room temperature for 1 hour, and heated under reflux for 2 hours with stirring. The mixture was filtered and the insoluble substances were washed with methanol and water. The filtrate and the washings were combined and evaporated under reduced pressure. The residue was dissolved in methanol (50 mL), to which Raney nickel (1.0 g) was added, and subjected to catalytic reduction at room temperature at the pressure of 3.5–4 kg/cm$^2$ overnight. The mixture was filtered and the catalysts were washed with methanol-water (1:4). The filtrate and the washings were combined and evaporated under reduced pressure. The residue was applied to a column of Amberlite CG-50 (NH$_4$ +form, 100 mL). The column was washed with water and then eluted with 0.1 N ammonium hydroxide. The eluate was evaporated under reduced pressure, and the residue was re-chromatographed on a column of Dowex 1×2 (OH$^-$ form, 30 mL) with water. The eluate was evaporated under reduced pressure, and lyophilized to give a white solid of valiolamine (35 mg).

$[\alpha]^{25}_D$+19.6° (c=1, H$_2$O); NMR (D$_2$O)δ:1.68 (1H, dd, J=3.8 Hz, 15.5 Hz, 6—CHax), 1.88 (1H, dd, J=2.9 Hz, 15.1 Hz, 6CHeq), 3.33 (1H, q*, J=2.9 Hz, 3.8 Hz, 4.2 Hz, 5-CH), 3.41 (1H, d, J=9.5 Hz, 2-CH), 3.44 and 3.52 (each 1H, ABq, J=11.3 Hz, —CH$_2$O—), 3.57 (1H, dd, J=4.2 Hz, 9.9 Hz, 4—CH), 3.85 (1H, t*, J=9.5 Hz, 9.9 Hz, 3-CH)(apparent splitting pattern).

Elemental analysis for $C_7H_{15}NO_5H_2O$:
Calc.(%): C, 39.80; H, 8.11; N, 6.63.
Found(%): C, 39.89; H, 8.19; N, 6.48.

EXAMPLE 5

(1S)-(1(OH),2,4,5/1,3)-5[[2-Hydroxy-1-(hydroxymethyl)ethyl]amino]-1-C-(hydroxymethyl)-1,2,3,4 -cyclohexanetetrol (1S)-(1(OH),2,4/1,3)-2,3,4-Tri-O-benzyl-1-C-(benzyloxymethyl)-5-oxo-6,6-(trimethylenedithio)-1,2,3,4-cyclohexanetetrol (1.0 g) and 2-amino-1,3-propanediol (0.16 g) were dissolved in N,N-dimethylformamide (20 mL), and stirred at room temperature for 30 minutes. Sodium cyanoborohydride (0.5 g) was added to the solution, and stirred at 60° C. overnight. The mixture was evaporated under reduced pressure, and the remaining solvent was removed by azeotropic distillation with toluene. The residue was partitioned between ethyl acetate and water. The ethyl acetate layer was washed with 2%(w/v) sodium chloride solution, dried over anhydrous magnesium sulfate, and evaporated under reduced pressure. A solution of the residue (1.05 g) in methanol (20 mL) was added to a suspension of Raney nickel (3 g) in methanol (20 mL) which was previously stirred in a stream of hydrogen at room temperature for 30 minutes, and heated under reflux for 1 hour with stirring. The mixture was filtered, and the insoluble substances were washed with methanol and water. The filtrate and the washings were combined and evaporated under reduced pressure. The residue was dissolved in methanol-water (4:1, 60 mL), to which Raney nickel (0.5 g) was added, and subjected to catalytic reduction at the pressure of 3.5–4 kg/cm$^2$ at room temperature overnight. The catalyst was filtered off and washed with methanol and water. The filtrate and the washings were combined and evaporated under reduced pressure. The residue was chromatographed on a column of Amberlite CG-50 ($NH_4^+$ form, 180 mL) with water. The eluate was evaporated under reduced pressure, and to the residue was added ethanol (5 mL). The mixture was heated under reflux for about 10 minutes, and then refrigerated to give white crystals (75 mg) of (1S)-(1(OH),2,4,5/1,3)-5-[[2-hydroxy-1-(hydroxymethyl)ethyl]amino]-1-C-(hydroxymethyl) -1,2,3,4-cyclohexanetetrol.

mp 162–163° C.; $[\alpha]^{25}_D +26.2°$ (c=1, $H_2O$).
Elemental analysis for $C_{10}H_{21}NO_7$:
Calc.(%): C, 44.94; H, 7.92; N, 5.24.
Found(%): C, 44.81; H, 8.05; N, 5.08.

EXAMPLE 6

(1S)-(1(OH),2,4/1,3)-2,3,4-Tri-O-(tetrahydropyranyl)-1-C-[(tetrahydropyranyl)oxymethyl]-5-oxo-6,6-(trimethyllenedithio)-1,2,3,4-cyclohexanetetrol and its (1R)(1(CH$_2$OH),2,4/1,3)-isomer A solution of trifluoroacetic anhydride (6.35 mL) in dichloromethane (65 mL) was added dropwise under cooling −65°—70° C. to a solution of dimethyl sulfoxide (4.42 mL) in dichloromethane (65 mL) and stirred at the same temperature for 30 minutes A solution of a mixture (5.18 g) of (1R)- and (1S)-isomers of 2,3,4,6-tetra-O-(tetrahydropyranyl)-1-C-(1,3-dithian-2-yl)-D-glucitol in dichloromethane (40 mL) was added dropwise to the mixture and stirred at −65°—70° C. for 1 hour. A solution of triethylamine (8.4mL) in dichloromethane (25 mL) was added dropwise to the mixture under cooling at the same temperature. After stirring for 15 minutes, the cooling bath was removed and the mixture was stirred to warm to 0° C. The reaction mixture was added to a mixture of dichloromethane (100 mL) and ice-water (150 mL). The dichloromethane layer was separated, washed with 2N hydrochloric acid, saturated sodium hydrogencarbonate solution and water, dried over anhydrous sodium sulfate, and evaporated to dryness under reduced pressure to give a colorless syrup of 2,3,4,6-tetra-O-(tetrahydropyranyl)-1-C-(1,3-dithian-2-yl)-D-xylo-5-hexosulose (5.0 g). The ketose derivative was dissolved in toluene (100 mL), to which potassium carbonate (4.1 g) and 18-crown-6 (0.1 g) were added, and stirred at room temperature for 15 hours. The mixture was filtered and the insoluble substances were washed with toluene (100 mL). The filtrate and the washings were combined, to which ethyl acetate (100 mL) and water (100 mL) were added, and stirred, and the organic layer was separated. The organic layer was washed with 2N hydrochloric acid, saturated sodium hydrogen carbonate and water, dried over anhydrous sodium sulfate, and evaporated under reduced pressure. The residue was chromatographed on a column of silica gel (400 mL). The column was eluted with toluene-ethyl acetate (4:1, 1.5 L) and then with toluene-ethyl acetate (1:1). The fraction eluted with toluene-ethyl acetate (4:1) (0.7–1.4 L) was evaporated to dryness under reduced pressure to give a light yellow solid (3.3 g). The solid was rechromatographed on a column of silica gel (250 mL). The column was washed with toluene (500 mL) and toluene-ethyl acetate (6:1, 1.4 L), and then eluted with toluene-ethyl acetate (2:1). The eluate was evaporated to dryness under reduced pressure to give a white solid (2.8 g) of (1S)-(1(OH),2,4/1,3)-2,3,4-tri-O-(tetrahydropyranyl)-1-C-[(tetrahydroxypyranyl) oxymethyl]-5-oxo-6,6-(trimethylenedithio)-1,2,3,4-cyclohexanetetrol.

IR ($CHCl_3$):1726 cm$^{-1}$.
Elemental analysis for $C_{30}H_{48}O_{10}S_2$:
Calc.(%): C, 56.94; H, 7.65; S, 10.13.
Found(%): C, 57.10; H, 7.84; S, 9.88.

The fraction (1.9–2.3 L) eluted with toluene-ethyl acetate (1:1) in the first chromatography was evaporated to dryness under reduced pressure to give a light yellow solid (1.05 g) supposed to be the (1R)-isomer.

IR ($CHCl_3$):1729 cm$^{-1}$.

EXAMPLE 7

(1S)-(1(OH),2,4/1,3)-2,3,4-Tri-O-benzyl-1-C-(benzyloxymethyl)-5-oxo-6,6-bis(methylthio)-1,2,3,4-cyclohexanetetrol 2,3,4,6-Tetra-O-benzyl-1-C-[bis(methylthio)methyl]-D-xylo-5-hexosulose (17.8 g), prepared by the procedure described in Reference Example 8, was applied to a column of silica gel (900 mL). The column was washed with toluene and eluted with toluene-ethyl acetate (9:1). The eluate was evaporated under reduced pressure, and the residue was rechromatographed on a column of silica gel with toluene-ethyl acetate (10:1). The eluate was evaporated under reduced pressure, and ethyl ether-petroleum ether (1:10, 300 mL) was added to the residue. The mixture was refrigerated overnight to give (1S)-(1(OH),2,4/1,3)-2,3,4-tri-O-benzyl-1-C-(benzyloxymethyl)-5-oxo-6,6-bis(methylthio)-1,2,3,4-cyclohexanetetrol (11.2 g) as white crystals.

mp 97°–98° C.; IR (KBr): 3324, 1732 cm$^{-1}$; $[\alpha]^{22}_D -35.6°$ (c=1, $CHCl_3$); NMR ($CDCl_3$)δ:1.83 (3H, s, $CH_3S$—), 2.12 (3H, s, $CH_3S$—), 2.86 (1H, s, —OH), 3.79 and 3.87 (each 1H, ABq, J=9.3 Hz, —CH₂O—), 4.08 (1H, t, J=9.3 Hz, 3-CH), 4.66 (1H, d, J=9.3 Hz, 2-CH); 4.43 (1H, d, J=11.8 Hz), 4.55 (1H, d, J=11.8 Hz), 4.65 (1H, d, J=11.3 Hz), 4.71 (1H, d, J=10.8 Hz), 4.79 (1H, d, J=10.8 Hz), 4.92 (1H, d, J=11.3 Hz) and 4.95 (2H, d, J=10.8 Hz)(PhCH₂—x 4); 5.05 (1H, d, J=9.3 Hz, 4-CH), 7.17-7.43 (20H, m, C₆H₅—x 4).

Elemental analysis for C₃₇H₄₀O₆S₂:
Calc.(%): C, 68.92; H, 6.25; S, 9.95.
Found(%): C, 69.11; H, 6.26; S, 10.07.

EXAMPLE 8

(1S)-(1(OH),2,4/1,3)-2,3,4-Tri-O-benzyl-1-C-(benzyloxymethyl)-5-oxo-6,6-bis(methylthio)-1,2,3,4-cyclohexanetetrol Sodium acetate (2.9 g) and 18-crown-6 (100 mg) was added to a solution of 2,3,4,6-tetra-O-benzyl-1-C-[bis(methylthio)methyl]-D-xylo-5-hexosulose (2.9 g), prepared by the procedure described in Reference Example 7, in toluene (100 mL) and then stirred for 18 hours at room temperature. The mixture was filtered off and insoluble materials were washed with toluene (50 mL). The filtrate and the washings were combined, washed with 2N hydrochloric acid and saturated sodium hydrogencarbonate solution, dried over anhydrous sodium sulfate, and then evaporated under reduced pressure Ethyl ether-petroleum ether (1:5, 60 mL) was added to the residue and the mixture was refrigerated overnight to give (1S)-(1(OH),2,4/1,3)-2,3,4-tri-O-benzyl-1-C-(benzyloxymethyl)-5-oxo-6,6-bis(methylthio)-1,2,3,4-cyclohexanetetrol (2.1 g) as white crystals.

Elemental analysis for C₃₇H₄₀O₆S₂:
Calc.(%): C, 68.92; H, 6.25; S, 9.95.
Found(%): C, 68.88; H, 6.19; S, 10.08.

EXAMPLE 9

(1S)-(1(OH),2,4/1,3)-2,3,4-Tri-0-benzyl-1-C-(benzyloxymethyl)5-oxo-1,2,3,4-cyclohexanetetrol To a solution of (1S)-(1(OH),2,4/1,3)-2,3,4-tri-O-benzyl-1-C-(benzyloxymethyl)-5-oxo-6,6-bis(methylthio)-1,2,3,4-cyclohexanetetrol (1.0 g) in dioxane (30 mL) was added Raney nickel (3.0 g), and the mixture was stirred for 30 minutes at room temperature. The insoluble materials were filtered off and washed with dioxane. The filtrate and the washings were combined, and evaporated under reduced pressure. The residue was chromatographed on a column of silica gel (100 mL) with toluene-ethyl acetate (6:1) The eluate was evaporated under reduced pressure and ethyl ether-petroleum ether (1:8, 10 mL) was added to the residue. The mixture was refrigerated overnight to give (1S)-(1(OH),2,4/1,3)-2,3,4-tri-O-benzyl-1-C-(benzyloxymethyl)-5-oxo-1,2,3,4-cyclohexanetetrol (320 mg) as white crystals.

mp 84°-85° C.; [α]²² $_D$ +45.1° (c=1, CHCl₃); IR (KBr): 3440, 1735 cm⁻¹; NMR (CDCl₃)δ:2.39 (1H, d, J=2.0 Hz, —OH), 2.47 (1H, d, J=14.5 Hz, 6-CHeq), 2.84 (1H, ddd, J=0.9 Hz, 2.0 Hz, 14.5 Hz, 6-CHax), 3.15 and 3.53 (each 1H, ABq, J=8.6H z, —CH₂O—), 4.01 (1H, t. J=9.0 Hz, 3-CH), 4.06 (1H, d, J=9.0 Hz, 2-CH), 4.14 (1H, dd, J=0.9 Hz, 9.0 Hz, 4-CH); 4.41 (1H, d, J=11.8 Hz), 4.47 (1H, d, J=11.8 Hz), 4.55 (1H, d, J=10.7 Hz), 4.56 (1H, d, J=11.7 Hz), 4.75 (1H, d, 15 J=10.7 Hz), 4.95 (1H, d, J=10.7 Hz), 4.96 (1H, d, J=11.7 Hz) and 4.99 (1H, d, J=10.7 Hz)(PhCH₂—x 4); 7.15-7.42 (20H, m, C₆H₅—x 4).

Elemental analysis for C₃₅H₃₆O₆:
Calc.(%): C, 76.06; H, 6.57.
Found(%): C, 75.98; H, 6.71.

EXAMPLE 10

(1S)-(1(OH),2,4,5/1,3)-5-[[2-Hydroxy-1-(hydroxymethyl)ethyl]amino]-1-C-(hydroxymethyl)-1,2,3,4-cyclohexanetetrol A solution of (1S)-(1(OH),2,4/1,3)-2,3,4-tri-O-benzyl-1-C-(benzyloxymethyl)-5-oxo-6,6-bis(methylthio)1,2,3,4-cyclohexanetetrol (1 0 g) and 2-amino-1,3-propanediol (0.2 g) in ethanol (20 mL) was stirred at room temperature for 4 hours, to which sodium cyanoborohydride (0.5 g) was added, and stirred at 60° C. overnight. The mixture was evaporated under reduced pressure, and the residue was partitioned between ethyl acetate and 5%(w/v) sodium chloride solution. The ethyl acetate layer was washed with water, dried over anyhydrous sodium sulfate, and evaporated under reduced pressure. A solution of the residue (1.0 g) in ethanol (20 mL) was added to a suspension of Raney nickel (3 g) in ethanol (30 mL) which was previously stirred at room temperature in a stream of hydrogen for 30 minutes, and heated under reflux for 30 minutes. The mixture was filtered and the insoluble substances were washed with methanol and water. The filtrate and the washings were combined, and evaporated under reduced pressure. The residue was dissolved in methanol-water (4:1, 80 mL), to which Raney nickel (0.5 g) was added, and subjected to catalytic reduction at the pressure of 3.5–4 kg/cm² at room temperature overnight. The catalyst was filtered off, and washed with methanol and water. The filtrate and the washings were combined and evaporated under reduced pressure. The residue was partitioned between water and ethyl ether, and the aqueous layer was evaporated under reduced pressure. The residue was chromatographed on a column of Amberlite CG-50 (NH₄⁺ form, 180 mL) with water. The eluate was evaporated under reduced pressure. Ethanol (5 mL) was added to the residue. The mixture was heated under reflux for about 10 minutes and refrigerated overnight to give (1S)-(1(OH),2,4,5/1,3)-5-[[2-hydroxy-1-(hydroxymethyl)ethyl]-amino]-1-C-(hydroxymethyl)-1,2,3,4-cyclohexanetetrol as white crystals (70 mg).

EXAMPLE 11

(1S)-(1(OH),2,4,5/1,3)-5-Amino-1-C-(hydroxymethyl)-1,2,3,4-cyclohexanetetrol (valiolamine)

Hydroxylamine hydrochloride (720 mg) and sodium acetate (1.4 g) were added to a solution of (1S)-(1(OH),2,4/1,3)-2,3,4-tri-O-benzyl-1-C-(benzyloxymethyl)-5-oxo-6,6-bis(methylthio)-1,2,3,4-cyclohexanetetrol (1.0 g) in methanol (50 mL), and stirred at room temperature for 15 days. The mixture was evaporated under reduced pressure, and the residue was partitioned between ethyl acetate and water. The ethyl acetate layer was washed with 2N hydrochloric acid and saturated sodium hydrogencarbonate solution, dried over anhydrous sodium sulfate, and evaporate under reduced pressure. A solution of the residue (1.1 g) in methanol (50 mL) was added to a suspension of Raney nickel (5 g) in methanol (50 mL) which was previously stirred in a stream of hydrogen for 1 hour, and then the mixture was heated under reflux with stirring for 1 hour. The mixture was filtered and the insoluble substances were washed with methanol and water. The filtrate and the washings were combined, and evaporated under reduced pressure. The residue was dissolved in methanol (50 mL), to which Raney nickel (0 g) was added, and subjected to catalytic reduction at the pressure of 3.5-4 kg/cm² at room temperature overnight. The mixture was filtered and the catalyst was washed with methanol and water. The filtrate and the washings were combined and evaporated under reduced pressure. The residue was chromatographed on a column of Amberlite CG-50 (NH₄⁺ form, 100 mL). The column was washed with water and eluted with 0.1N ammonium hydroxide. The eluate was rechromatographed on a column of Dowex 1×2 (OH⁻ form, 50 mL) with water. The eluate was concentrated under reduced pressure and freeze-dried to give valiolamine as a white solid.

EXAMPLE 12

(1S)-(1(OH),2,4/1,3)-2,3,4-Tri-O-benzyl-1-C-(benzyloxymethyl)-6,6-dichloro-5-oxo-1,2,3,4-cyclohexanetetrol To a solution of dimethyl sulfoxide (7.4 mL) in dichloromethane (80 mL) was added dropwise a solution of trifluoroacetic anhydride (9.6 mL) in dichloromethane (40 mL) at $-65°$ - $-75°$ C., and stirred at the same temperature for 30 minutes. To the solution was added dropwise a solution of 2,3,4,6-tetra-O-benzyl-1-C-(dichloromethyl)-D-glucitol (10.6 g) in dichloromethane (60 mL) at $-65°$ - $-75°$ C. and stirred at the same temperature for 1 hour. To this mixture was added dropwise a solution of triethylamine (19 mL) in dichloromethane (80 mL) under cooling below -65° C., and stirred for 15 minutes. The cooling bath was removed and the mixture was stirred to warm to 0° C. To the mixture were added ice-cooled dichloromethane (400 mL) and water (200 mL) and stirred, and then the dichloromethane layer was separated. The dichloromethane layer was washed with 2N hydrochloric acid and saturated sodium hydrogencarbonate solution, dried over anhydrous sodium sulfate, and evaporated under reduced pressure. To the residue was added ethyl ether-petroleum ether (1:10, 110 mL) and refrigerated overnight to give (1S)-(1(OH),2,4/1,3)-2,3,4-tri-O-benzyl-1-C-(benzyloxymethyl)-6,6-dichloro-5-oxo-1,2,3,4-cyclohexanetetrol as white crystals (7.03 g).

mp 139°–142° C.; $[\alpha]^{23}_D$ +2.5° (c=1, CHCl₃); IR (KBr): 3410, 1760 cm⁻¹; NMR (CDCl₃) δ:3.30 (1H, s), 3.84 (2H, s), 4.05 (1H, t, J=9.5 Hz), 4.31 (1H, d, J=9.5 Hz), 4.50 –5.05 (9H, m), 7.15–7.45 (20H, m).

Elemental analysis for $C_{35}H_{34}Cl_2O_6$:
Calc.(%): C, 67.63; H, 5.51; Cl, 11.41.
Found(%): C, 68.00; H, 5.53; Cl, 11.39.

EXAMPLE 13

(1S)-(1(OH),2,4/1,3)-2,3,4-Tri-O-benzyl-1-C-(benzyloxymethyl)-6,6-dichloro-5-oxo-1,2,3,4-cyclohexanetetrol A solution of n-butyllithium in n-hexane (1.6M solution, 7.5 mL) was added dropwise to a solution of diisopropylamine (16.8 mL) in tetrahydrofuran (100 mL) under positive pressure of an argon gas at $-10°$ to $-20°$ C. with stirring and then stirred for 1 hour at the same temperature. The solution was added to a solution of 2,3,4,6-tetra-O-benzyl-D-glucono-δ-lactone (21.6 g) in dichloromethane (80 mL) under positive pressure of an argon gas at $-70°$ to $-75°$ C. with stirring and then stirred for 1 hour at the same temperature. The mixture was partitioned between dichloromethane (350 mL) and 2N hydrochloric acid with ice-cooling. The organic layer was separated and washed with water and then saturated sodium hydrogencarbonate solution, and dried over anhydrous sodium sulfate. The organic layer was evaporated to dryness under reduced pressure to give crude 2,3,4,6-tetra-O-benzyl-1-C-(dichloromethyl)-D-glucopyranose (26.6 g) as a syrup. The syrup (26.6 g) was dissolved in tetrahydrofuran-diethylene glycol dimethyl ether (1:1, 265 mL). Sodium borohydride (10.0 g) was added to the solution with cooling (ice-water bath). The mixture was stirred for 30 minutes with cooling and then overnight at room temperature. The mixture was evaporated under reduced pressure and the residue was partitioned between ethyl acetate (1.2 L) and water (600 mL). The ethyl acetate layer was washed with 2N hydrochloric acid and saturated sodium hydrogencarbonate solution, dried over anhydrous sodium sulfate, and then evaporated under reduced pressure to dryness to give a mixture of crude (1S)- and (1R)-isomers of 2,3,4,6-tetra-O-benzyl-1-C-(dichloromethyl)-D-glucitol (26.9 g) as a colorless or light yellow syrup. This syrup was used for the next step without further purification.

A solution of trifluoroacetic anhydride (24.2 mL) in dichloromethane (75 mL) was added dropwise to a solution of dimethyl sulfoxide (18.6 mL) in dichloromethane (75 mL) with stirring at $-65°$ to $-75°$ C. and then for 30 minutes at the same temperature. To the mixture was added dropwise a solution of 2,3,4,5,6-tetra-O-benzyl-1-C-(dichloromethyl)-D-glucitol (26.9 g) in dichloromethane (125 mL) with stirring at $-65°$ to $-75°$ C. and then stirred for 1 hour at the same temperature. A solution of triethylamine (48 mL) in dichloromethane (150 mL) was added dropwise with stirring. at temperatures below $-65°$ C. The cooling bath was removed and the mixture was allowed to warm to 0° C. with stirring Ice-cooling dichloromethane (100 mL) and water (400 mL) were added to the mixture. The mixture was stirred and then the dichloromethane layer was separated. The dichloromethane layer was washed with 2N hydrochloric acid and saturated aqueous sodium hydrogencarbonate, dried over anhydrous sodium sulfate, and then evaporated under reduced pressure. Ethyl ether-petroleum ether (1:10, 250 mL) was added to the mixture and the mixture was allowed to stand at room temperature overnight to give (1S)-(1(OH),2,4/1,3)-2,3,4-tri-O-benzyl-1-C-(benzyloxymethyl)-6,6-dichloro-5-oxo-1,2,3,4-cyclohexanetetrol (15.6 g) as white crystals.

EXAMPLE 14

(1S)-(1(OH),2,4,5/1,3)-5-[[2-Hydroxy-1-(hydroxymethyl)ethyl]amino]-1-C-(hydroxymethyl)-1,2,3,4-cyclohexanetetrol Palladium black (250 mg) was added to a solution of (1S)-(1(OH),2,4/1,3)-2,3,4-tri-O-benzyl-1-C-(benzyloxymethyl)-6,6-dichloro-5-oxo-1,2,3,4-cyclohexanetetrol (500 mg) and 2-amino-1,3-propanediol (210 mg) in tetrahydrofuran-methanol (1:1, 80 mL), and the mixture was subjected to catalytic reduction at the pressure of 3.5–4 kg/cm² at room temperature overnight. Acetic acid (0.25 mL), water (5 mL) and palladium black (300 mg) were added to the mixture, which was subjected to catalytic reduction at the pressure of 3.5–4 kg/cm² at room temperature overnight. The mixture was filtered, and the catalyst was washed with 50% methanol-water and water. The filtrate and the washings were combined, and evaporated under reduced pressure. The residue was partitioned between water (150 mL) and ethyl acetate (100 mL). The aqueous layer was evaporated under reduced pressure, and the residue was chromatographed on a column of Amberlite CG-50 (NH₄⁺ form, 180 mL) with water. The eluate was evaporated under reduced pressure. Ethanol (5 mL) was added to the residue, and the mixture was heated under reflux for about 10 minutes and refrigerated overnight to give (1S)-(1(OH), 2,4,5/1,3)-5-[[2-hydroxy-1-(hydroxymethyl)ethyl]amino]-1-C-(hydroxymethyl)-1,2,3,4-cyclohexanetetrol as white crystals.

$[\alpha]^{25}_D 26.2°$ (c=1, H$_2$O); NMR (D$_2$O)δ:1.54 (1H, dd, J=3 Hz, 15 Hz), 2.09 (1H, dd, J=3.5 Hz, 15 Hz), 2.89 (1H, quint, J=5.5 Hz), 3.3–4.0 (10H, m).

Elemental analysis for C$_{10}$H$_{21}$NO$_7$:
Calc.(%): C, 44.93; H, 7.92; N, 5.24.
Found(%): C, 44.82; H, 8.09; N, 5.13.

EXAMPLE 15

(1S)-(1(OH),2,4,6/1,3)-2,3,4-Tri-O-benzyl-1-C-(benzyloxymethyl)-6-chloro-5-oxo-1,2,3,4-cyclohexanetetrol Zinc dust (2.0 g) was added by portions to a suspension of (1S)-(1(OH),2,4/1,3)-2,3,4-tri-O-benzyl-1-C-(benzyloxymethyl)-6,6-dichloro-5-oxo-1,2,3,4-cyclohexanetetrol (2.0 g) in acetic acid (10 mL) by keeping the reaction temperature at 15°–20° C., and stirred at the same temperature for 1 hour. To the mixture was added ethyl ether (50 mL), and the resulting precipitate was filtered and washed with ethyl ether (50 mL). The filtrate and the washings were combined, washed with water and saturated sodium hydrogencarbonate solution, dried over anhydrous sodium sulfate, and evaporated under reduced pressure Ethyl ether-petroleum ether (1:5, 60 mL) was added to the residue and the mixture was allowed to stand at room temperature overnight to give (1S)-(1(OH),2,4,6/1,3)-2,3,4-tri-O-benzyl-1-C-(benzyloxymethyl)-6-chloro-5-oxo-1,2,3,4-cyclohexanetetrol as white crystals (1.24 g).

mp 103.5°–106° C.; $[\alpha]^{24}_D +62.6°$ (c=1, CHCl$_3$); IR (KBr): 3470, 1759 cm$^{-1}$; NMR (CDCl$_3$)δ:2.23 (1H, broad s), 3.53 and 3.66 (1H each, ABq, J=10 Hz), 3.97–4.25 (3H, m), 4.40–5.05 (9H, m), 7.1–7.5 (20H, m).

Elemental analysis for C$_{35}$H$_{35}$ClO$_6$:
Calc.(%): C, 71.60; H, 6.01; Cl, 6.04.
Found(%): C, 71.63; H, 5.99; Cl, 6.00.

EXAMPLE 16

(1S)-(1(OH),2,4,5/1,3)-5-[[2-Hydroxy-1-(hydroxymethyl)ethyl]amino]-1-C-(hydroxymethyl)-1,2,3,4-cyclohexanetetrol Palladium black (150 mg) was added to a solution of (1S)-(1(OH),2,4,6/1,3)-2,3,4-tri-0-benzyl-1-C-(benzyloxymethyl)-6-chloro-5-oxo-1,2,3,4-cyclohexanetetrol (300 mg) and 2-amino-1,3-propanediol (100 mg) in methanol-acetic acid (9:1, 30 mL), and the mixture was subjected to catalytic reduction at the pressure of 3.7–3.9 kg/cm$^2$ at room temperature overnight. The catalyst was filtrated and washed with water and methanol. The filtrate and the washings were combined and evaporated under reduced pressure, and the residue was partitioned between water and ethyl ether. The aqueous layer was evaporated under reduced pressure, and the residue was chromatographed on a column of Amberlite CG-50 (NH$_4$$^+$ form, 170 mL) with water. The eluate was evaporated under reduced pressure, and ethanol (10 mL) was added to the residue. The mixture was heated under reflux for about 10 minutes, and refrigerated overnight to give (1S)-(1(OH),2,4,5/1,3)-5-[[2-hydroxy-1-(hydroxymethyl)ethyl]amino]-1-C-(hydroxymethyl)-1,2,3,4-cyclohexanetetrol as white crystals (50 mg).

EXAMPLE 17

(1S)-(1(OH),2,4/1,3)-2,3,4-Tri-O-benzyl-1-C-(benzyloxymethyl)-6,6-dibromo-5-oxo-1,2,3,4-cyclohexanetetrol A solution of trifluoroacetic anhydride (1.93 mL) in dichloromethane (8.2 mL) was added dropwise to a solution of dimethyl sulfoxide (1.5 mL) in dichloromethane (8.2 mL) at −65°––70° C., and stirred at the same temperature for 30 minutes. To the solution was added dropwise a solution of 2,3,4,6-tetra-O-benzyl-1-C-(dibromomethyl)-D-glucitol (2.13 g) in dichloromethane (12.3 mL) at −65°––70° C., and stirred at the same temperature for 1 hour. A solution of triethylamine (3.81 mL) in dichloromethane (16.4 mL) was added dropwise to the mixture at the same temperature, and stirred for 15 minutes The cooling bath was removed and the mixture was stirred to warm to 0° C. The mixture was added to ice-cooled dichloromethane (100 mL) and water (50 mL) for partition, and then the organic layer was separated. The organic layer was washed with 2N hydrochloric acid and saturated sodium hydrogencarbonate solution, dried over anhydrous sodium sulfate, and evaporated under reduced pressure The residue was chromatographed on a column of silica gel (250 mL) with toluene-ethyl acetate (20:1). The eluate was evaporated under reduced pressure to give (1S)-(1(OH),2,4/1,3)-2,3,4-tri-0-benzyl-1-C-(benzyloxymethyl)-6,6-dibromo-5-oxo-1,2,3,4-cyclohexanetetrol as a colorless syrup (690 mg).

IR(CHCl$_3$):3494, 1747 cm$^{-1}$.

EXAMPLE 18

(1S)-(1(OH),2,4/1,3)-2,3,4-Tri-O-benzyl-1-C-(benzyloxymethyl)-5-oxo-1,2,3,4-cyclohexanetetrol (a) A solution of (1S)-(1(OH),2,4/1,3)-2,3,4-tri-O-benzyl-1-C-(benzyloxymethyl)-5-oxo-6,6-dichloro-1,2,3,4-cyclohexanetetrol (3.0 g), tributyltin hydride (5.0 g) and α,α'-azobis-iso-butyronitrile (0.3 g) in toluene (30 mL) was heated at 100° C. for 1 hour with stirring. After cooling to room temperature, ethyl acetate (150 mL) was added to the mixture. The organic solution was washed with 2N hydrochloric acid and saturated sodium hydrogencarbonate solution, dried over anhydrous sodium sulfate, and then evaporated under reduced pressure. The residue was chromatographed on a column of silica gel (250 mL) with toluene-ethyl acetate (6:1). The eluate was evaporated under reduced pressure and ethyl ether-petroleum ether (1:6, 35 mL) was added to the residue. The mixture was refrigerated overnight to give (1S)-(1(OH),2,4/1,3)-2,3,4-tri-O-benzyl-1-C-(benzyloxymethyl)-5-oxo-1,2,3,4-cyclohexanetetrol (1.87 g) as white crystals.

mp 84°–85° C.; $[\alpha]^{22}_D +45.1°$ (c=1, CHCl$_3$); IR (KBr): 3440, 1735 cm$^{-1}$; NMR (CDCl$_3$)δ:2.45 (1H, d, J=15 Hz), 2.82 (1H, d, J=15 Hz), 3.15 (1H, d, J=9 Hz), 3.53 (1H, d, J=9 Hz), 3.95–4.15 (3H, m), 4.40–5.05 (8H, m), 7.05–7.55 (20H, m); NMR (CDCl$_3$, 300 MHz) δ:2.39 (1H, d, J=2.0 Hz, —OH), 2.47 (1H, d, J=14.5 Hz, 6-CHeq), 2.84 (1H, ddd, J=0.9 Hz, 2.0 Hz, 14.5 Hz, 6-CHax), 3.15 and 3.53 (each 1H, ABq, J=8.6H z, —CH$_2$O—), 4.01 (1H, t, J=9.0 Hz, 3-CH), 4.06 (1H, d, J=9.0 Hz, 2-CH), 4.14 (1H, dd, J=0.9 Hz, 9.0 Hz, 4-CH); 4.41 (1H, d, J=11.8 Hz), 4.47 (1H, d, J=11.8 Hz), 4.55 (1H, d, J=10.7 Hz), 4.56 (1H, d, J=11.7 Hz), 4.75 (1H, d, J=10.7 Hz), 4.95 (1H, d, J=10.7 Hz), 4.96 (1H, d, J=11.7 Hz) and 4.99 (1H, d, J=10.7 Hz)(PhCH$_2$—x 4); 7.15–7.42 (20H, m, C$_6$H$_5$—x 4).

Elemental Analysis for $C_{35}H_{36}O_6$:
Calc.(%): C, 76.06; H,6.57.
Found(%): C, 76.11; H,6.47.

(b) To a solution of (1S)-(1(OH),2,4/1,3)-2,3,4-Tri-O-benzyl-1-C-(benzyloxymethyl)-5-oxo-6,6-dichloro-1,2,3,4-cyclohexanetetrol (2.0 g) in tetrahydrofuran-methanol (1:7, 80 mL) were added 5%(w/w) palladium-barium sulfate (0.5 g) and sodium acetate (2.0 g), and the mixture was hydrogenated overnight at the pressure of 3-3.5 kg/cm² at room temperature. The mixture was filtered off and the catalysts were washed with tetrahydrofuran and methanol. The filtrate and the washings were combined and evaporated under reduced pressure. The residue was partitioned between ethyl acetate (100 mL) and water (40 mL). The organic layer was washed with 2N hydrochloric acid and saturated sodium hydrogencarbonate solution, dried over anhydrous sodium sulfate, and then evaporated under reduced pressure. The residue was chromatographed on a column of silica gel (250 mL) with toluene-ethyl acetate. The eluate was evaporated under reduced pressure, and ethyl ether-petroleum ether (1:10, 30 mL) was added to the residue. The mixture was refrigerated overnight to give (1S)-(1(OH),2,4/1,3)-2,3,4-trio-O-benzyl-1-C-(benzyloxymethyl)-5-oxo-1,2,3,4-cyclohexanetetrol (710 mg) as white crystals.

We claim:
1. A process of preparing an inosose compound represented by the formula

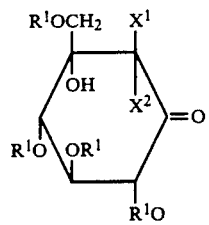

wherein $X^1$ and $X^2$ are both halogen; or $X^1$ is $-SQ^1$ and $X^2$ is $-SQ^2$ (each of $Q^1$ and $Q^2$ is lower alkyl or $Q^1$ and $Q^2$ may form lower alkylene) and $R^1$ is a protective group for hydroxyl, which comprises treating a compound represented by the formula

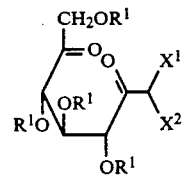

wherein $X^1$ and $X^2$ are both halogen; or $X^1$ is $-SQ^1$ and $X^2$ is $-SQ^2$ (each of $Q^1$ and $Q^2$ is lower alkyl or $Q^1$ and $Q^2$ may form lower alkylene) and $R^1$ is a protective group for hydroxyl, with a base or silica gel at about $-78°$ C. to the boiling point of a solvent included therewith for about 1 to 18 hours.

* * * * *